United States Patent [19]

Maiti et al.

[11] Patent Number: 5,439,904
[45] Date of Patent: Aug. 8, 1995

[54] 2-SPIRO(2'-SPIROCYCLOALKYL)CYCLO-PROPYL CEPHALOSPORIN SULFONES AS ANTIINFLAMMATORY AND ANTIGENERATIVE AGENTS

[75] Inventors: Samarendra N. Maiti; Charles Y. Fiakpui; Andhe V. N. Reddy; David P. Czajkowski; Ronald G. Micetich, all of Alberta, Canada

[73] Assignee: Synphar Laboratories, Inc., Alberta, Canada

[21] Appl. No.: 162,478

[22] Filed: Dec. 7, 1993

[51] Int. Cl.$^6$ .................. C07D 501/59; A61K 31/545
[52] U.S. Cl. ..................... 514/200; 514/202; 514/203; 514/204; 540/222; 540/226; 540/227; 540/215
[58] Field of Search ............... 514/200, 202, 203, 204; 540/215, 228, 230, 221

[56] References Cited

U.S. PATENT DOCUMENTS

| | | | |
|---|---|---|---|
| 4,547,371 | 10/1985 | Doherty et al. | 514/200 |
| 5,264,429 | 11/1993 | Maiti et al. | 540/222 |

FOREIGN PATENT DOCUMENTS

| | | |
|---|---|---|
| 80624/87 | 11/1987 | Australia . |
| 32762/89 | 4/1989 | Australia . |
| 0124081A2 | 5/1983 | European Pat. Off. . |
| 0267723A2 | 11/1986 | European Pat. Off. . |
| 0337704A2 | 4/1988 | European Pat. Off. . |
| 0457381A2 | 4/1991 | European Pat. Off. . |
| 89/10926 | 11/1989 | WIPO . |

OTHER PUBLICATIONS

Nature, vol. 322, pp. 192–194 (1986), by J. B. Doherty et al.
Tet. Letts., vol. 32, pp. 6207–6210 (1991).
J. Med. Chem, vol. 33, pp. 2513–2521 (1990).
J. Med. Chem., vol. 33, pp. 2522–2528 (1990).
J. Med. Chem., vol. 33, pp. 2529–2535 (1990).
Biochemistry, vol. 31, pp. 4980–4986 (1992).
J. Org. Chem., vol. 54, pp. 3907–3913 (1989).
Eur. J. Med. Chem., vol. 24, pp. 599–604 (1989).
J. Cellular Biochem., vol. 39, pp. 47–53 (1989).
Am. Rev. Respir. Dis., vol. 141, pp. 672–677 (1990).
Nature, vol. 327, pp. 79–82 (1987).
J. Med. Chem., vol. 35, pp. 3731–3744 (1992).
Eur. J. Med. Chem., vol. 27, pp. 875–890 (1992).
Bioorganic & Medicinal Chemistry Letters, vol. 2, pp. 1127–1132 (1992).
Heterocycles, vol. 36, pp. 1747–1762 (1993).

*Primary Examiner*—Nicholas Rizzo
*Attorney, Agent, or Firm*—Nikaido, Marmelstein, Murray & Oram

[57] ABSTRACT

2-spiro (2'-spirocycloalkyl) cyclopropyl cephalosporin sulfone compounds, methods of treating patients for elastase inhibition, and processes for preparing such compounds.

12 Claims, No Drawings

2-SPIRO(2'-SPIROCYCLOALKYL)CYCLOPROPYL CEPHALOSPORIN SULFONES AS ANTIINFLAMMATORY AND ANTIGENERATIVE AGENTS

FIELD OF THE INVENTION

The present invention relates to novel 2-spiro (2'-spirocycloalkyl)cyclopropyl cephalosporin sulfone derivatives as potent elastase inhibitors and to processes for their preparation.

BACKGROUND OF THE INVENTION

Human leukocyte elastase (HLE) is a member of the family of serine proteases. It is carried by the azurophilic granules of human polymorphonuclear leukocytes and released into the extracellular space. Elastase, like other serine proteases, have a catalytic triad composed of three juxtaposed amino acid residues :aspartate (Asp-102), histidine (His-57), and serine (Ser-195). Through either a "charge relay" or a "proton relay" mechanism, the three residues catalyze a proton extraction via oxyanion attack (ser-195) on an amide carbonyl group. The end result of this reaction is a degradation of peptide bonds.

Under normal conditions, the proteolytic activity of HLE is controlled by several natural protease inhibitors. The primary guardian against connective tissue destruction is $\alpha$-1 protease inhibitor ($\alpha$-PI). Although $\alpha$-PI associates with HLE very quickly and irreversibly, several pathological conditions may arise when $\alpha$-PI levels are genetically low, or when $\alpha$-PI has been oxidized or degraded, or when access to HLE is restricted. The disease states resulting from uncontrolled elastase activity include: pulmonary emphysema, rheumatoid arthritis, adult respiratory distress syndrome (ARDS), cystic fibrosis, and other related syndromes.

SUMMARY OF THE INVENTION

The present inventors synthesized 7 $\alpha$-substituted 2-spiro(2'-spirocyclo- alkyl)- cyclopropyl cephem sulfones and found from studies that these compounds are potent elastase inhibitors and that they are useful in the prevention, control and treatment of inflammatory conditions, particularly rheumatoid arthritis, osteoarthritis, cystic fibrosis, chronic bronchitis and emphysema.

DETAILED DESCRIPTION OF THE INVENTION

In accordance with the present invention, there is provided novel 7 $\alpha$-substituted 2-spiro(2'-spirocycloalkyl)cyclopropyl cephalosporin sulfones having anti-elastase activity. Such derivatives, or elastase inhibitors, are useful in the prevention, control and treatment of inflammatory conditions, particularly emphysema, rheumatoid arthritis, osteoarthritis and cystic fibrosis, chronic bronchitis and emphysema.

In one aspect, the present invention relates to a 7 $\alpha$-substituted 2-spiro(2'-spirocycloalkyl)cyclopropyl cephalosporin sulfone of the structural formula (I):

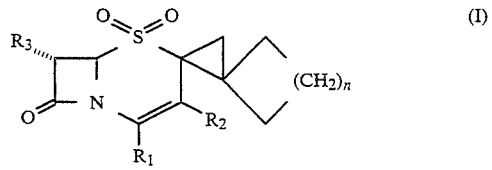

Wherein $R_1$ is $COOR_4$, $COR_5$, $-C(R_5)=N-O_6$, $CONR_7R_8$ $R_4$ is hydrogen; $C_{1-6}$ branched or straight alkyl; $C_{2-6}$ alkenyl; $CB_{1-6}$ alkanoyl $C_{1-6}$ alkyl; $C_{1-6}$ alkanoyloxy $C_{1-6}$ alkyl; $C_{1-6}$ alkoxy $C_{1-6}$ alkyl; halogenated $C_{1-6}$ alkyl; $-CH_2$-phenyl; $-CH(phenyl)_2$; the phenyl groups may further be substituted with at least one of $C_{1-6}$alkyl, $C_{10-}$alkoxy, nitro.

The preferred groups representing $R_5$ include hydrogen, methyl, ethyl, tert-butyl, allyl, methoxyethyl, benzhydryl, benzyl, p-nitrobenzyl, p-methoxybenzyl, 2,2,2-trichloroethyl.

$R_5$ is hydrogen; $C_{1-6}$ straight or branched alkyl; $C_{2-6}$alkenyl; $C_{2-6}$alkynyl; $C_{3-6}$ cycloalkyl; $C_{6-10}$ aryl; aralkyl; a monocyclic or fused polycyclic saturated or unsaturated heterocyclic group containing from 1 to 4 of any one or more of the heteroatoms selected from N, S and O.

The preferred groups representing $R_5$ include hydrogen, methyl, ethyl, n-propyl, iso-propyl, n-butyl, iso-butyl, tert-butyl, cyclopropyl, cyclobutyl, cyclopentyl, cyclohexyl, ethenyl, propenyl, ethynyl, phenyl, benzyl, thienyl, furyl, pyridyl, pyrimidinyl, imidazolyl, triazinyl, triazolyl, tetrazolyl, thiazolyl, thiadiazolyl.

The substituent $R_5$ in the formula $-C(R_5)=N-OR_6$ has the same meaning as described above.

The substituent $R_6$ is hydrogen or a hydrocarbon residue which may be substituted. In the formula $-C(R_5)=N-OR_6$, the $OR_6$ group may be in "syn" or "anti" configuration. The hydrocarbon residue may be exemplified by $C_{1-6}$ straight or branched alkyl, $C_{2-6}$ alkenyl and $C_{3-6}$ cycloalkyl group.

Substituents of these hydrocarbon residues may be exemplified by hydroxyl group, $C_{3-6}$ cycloalkyl group, mercapto group, amino group, halogen atom, cyano group, carboxyl group, $C_{1-8}$alkoxycarbonyl group, $C_{6-10}$ aryloxycarbonyl group, $C_{7-12}$ aralkyloxycarbonyl group, $C_{3-5}$ alkenyloxycarbonyl group, $C_{6-10}$aryl group, a 5- (or 6-) membered heterocyclic group containing from 1 to 4 of any one or more of the heteroatoms selected from N, S and O (examples of which include but are not limited to thienyl, furyl, pyridyl, pyrimidinyl, thiazolyl, isothiazolyl, thiadiazolyl, oxazolyl, isoxazolyl, imidazolyl, triazolyl, tetrazolyl, and the like).

The number of the substituents on the above mentioned hydrocarbon residue is not restricted to one and may be plural which are the same or different.

More preferred examples of the substituted hydrocarbon residues include $C_{1-3}$ alkyl groups substituted by halogen, hydroxy, amino, carboxyl, $C_{1-6}$ alkoxycarbonyl. Examples of the substituted hydrocarbon residues include 2-hydroxyethyl, 2-aminoethyl, 2-fluoroethyl, 2-chloroethyl, 2-bromoethyl, carboxymethyl, 1-carboxy-1-methylethyl, 1-carboxycyclopropyl, 1-carboxycyclobutyl, methoxycarbonylmethyl, ethoxycarbonylmethyl, tertbutoxycarbonylmethyl, 1-methoxycarbonyl-1-methylethyl, 1-ethoxycarbonyl-1-methylethyl, 1-tert-butoxycarbonyl-1-methyl-ethyl, 1- benzyloxycarbonyl-1-methylethyl, 1-pivaloyloxycarbonyl-1-methylethyl.

$R_7$ is hydrogen; $C_{1-6}$ alkyl; $C_{3-6}$ cycloalkyl; $C_{6-10}$ aryl; $C_{7-12}$ aralkyl; $C_{1-6}$ alkoxycarbonyl $C_{1-6}$ alkyl; carboxyl $C_{1-6}$ alkyl; a five or six-membered heterocyclic group containing from 1 to 4 of any one or more of the heteroatoms selected from N, O and S (examples of which include but are not limited to pyridyl, pyrimidinyl, pyrazinyl, triazinyl, imidazolyl, thiazolyl, isothiazolyl, thiadiazolyl, benzothiazolyl, oxazolyl, isoxazolyl, benzoxazolyl, benzimidazolyl, triazolyl, tetrazolyl, and the like).

$R_8$ is also selected from the above mentioned substituents as defined for $R_7$; however, they may be the same or different.

$R_7$ and $R_8$ in the formula $CONR_7R_8$ may combine to form a heterocyclic ring which may contain at least another heteroatom selected from N, S or O (examples of which include but are not limited to piperazinyl, morpholinyl, thiomorpholinyl, piperidinyl, pyrrolidinyl, and the like). The said heterocyclic ring may be substituted at the carbon atom or at the nitrogen atom which is different from the nitrogen atom having binding arm with the CO group in the formula $CONR_7R_8$. Examples of such substituents include hydroxyl, hydroxy $C_{1-4}$ alkyl, $C_{1-6}$ alkyl, $C_{2-6}$ alkenyl, $C_{2-6}$ alkynyl, $C_{3-6}$ cycloalkyl, $C_{1-6}$ alkoxy, $C_{1-6}$ alkoxy $C_{1-4}$ alkyl, azido, cyano, halogeno $C_{1-4}$ alkyl, carboxyl, carboxy $C_{1-4}$ alkyl, $C_{1-8}$ alkoxycarbonyl, $C_{1-8}$ alkoxycarbonyl $C_{1-4}$ alkyl, azido $C_{1-4}$ alkyl, cyano $C_{1-4}$ alkyl, amino, guanidino, amino $C_{1-4}$ alkyl, mono-$C_{1-4}$ alkylamino, di-$C_{1-4}$ alkylamino, mono-$C_{1-4}$ alkylamino $C_{1-4}$ alkyl, di-$C_{1-4}$ alkylamino $C_{1-4}$ alkyl, halogen atom, carbamoyl, diethoxyphosphinyl $C_{1-4}$ alkyl, dihydroxyphosphinyl $C_{1-4}$ alkyl, mercapto, mercapto $C_{1-6}$ alkyl, sulfo, sulfo $C_{1-4}$ alkyl, $C_{1-6}$ alkylthio, $C_{1-6}$ alkylthio $C_{1-4}$ alkyl, $C_{6-10}$ arylthio, $C_{6-10}$ aryloxycarbonyl, $C_{7-12}$ aralkyloxycarbonyl, $C_{1-5}$ alkanoyl, $C_{2-5}$ alkanoyl $C_{1-4}$ alkyl, $C_{2-5}$ alkanoyloxy, $C_{2-5}$ alkanoyloxy $C_{1-4}$ alkyl, or a heterocyclic group.

There may be the same or different plural of the above mentioned substituents, without limiting to the case of single substituent. The heterocyclic group means a 5- or 6-membered ring containing one to several heteroatoms, such as nitrogen atom (which may be oxidized), oxygen atom or sulfur atom, or a condensed ring thereof, which possesses a binding arm at the carbon atom.

More specifically, the above substituents are: hydroxy, carboxy, tert-butoxycarbonyl, azido, amino hydroxymethyl, hydroxyethyl, bromoethyl, cyano, carboxamide, guanidino, diethylphosphinylmethyl, diethylphosphinylethyl, dihydroxyphosphinylmethyl, dihydroxyphosphinylethyl, 1,2,3-triazole, tetrazole.

In the structural formula (I), $R_2$ is hydrogen, chloro, bromo, fluoro, hydroxy, $C_{1-6}$ alkoxy, trifluoromethyl, $C_{1-6}$ alkyl, $C_{2-6}$ alkenyl, $C_{2-6}$ alkynyl, $C_{3-6}$ cycloalkyl, or -$CH_2X$, wherein X is hydroxy, chloro, bromo, $C_{1-6}$ alkoxy, $C_{1-6}$ alkanoyloxy, -$OCONH_2$, -$OCONHC_{1-6}$ alkyl, amino, -$NHC_{1-6}$ alkyl, -$N(C_{1-6}$ alkyl$)_2$, a quaternary ammonium group (for example, $$\overset{\oplus}{NH_3}, \overset{\oplus}{NHZ_2}, \overset{\oplus}{NZ_3}$$

where Z represents lower alkyl, aryl or aralkyl; the nitrogen atom may also be the part of the heterocyclic system).

In the structural formula (I), $R_2$ also represents -$CH_2YR_9$, wherein Y is S or N.

When Y is sulfur, $R_9$ may be hydrogen or the residue of a thiol compound. The term "residue of a thiol compound" means a residue obtained by omitting the -SH group from a thiol compound. Preferred thiol compounds are heterocyclic thiols. Examples of such heterocyclic groups that might be mentioned are: an unsaturated 5 to 8 membered heteromonocyclic group containing at least one of the heteroatoms selected from N, O or S; an unsaturated 5 to 8 membered heteromonocyclic group containing 2 to 4 nitrogen atoms; an unsaturated 5 to 8 membered heteromonocyclic group containing 1 to 2 sulfur atoms and 1 to 3 nitrogen atoms; an unsaturated 5 to 8 membered heteromonocyclic group containing 1 to 2 oxygen atoms and 1 to 3 nitrogen atoms.

The above mentioned heterocyclic rings may be substituted further with one or more of the following radicals such as $C_{1-6}$ alkyl, -COOH, -COOC$_{1-6}$ alkyl, -OH, -$CH_2COOH$, -$CH_2COOC_{1-6}$ alkyl halogen, or the like. The substituents may be at the carbon atom or at the nitrogen atom.

In the formula -$CH_2YR_9$, when Y is nitrogen, $R_9$ represents the residue of a nitrogen containing heterocyclic ring system. More specifically, Y together with $R_9$ forms a heterocyclic ring where Y is nitrogen which is part of the heterocyclic system. The above mentioned heterocycles may be further substituted with one or more of the functional groups selected from chloro, bromo, fluoro, hydroxy, carboxy, carbomethoxy, carboethoxy, cyano, amino, hydroxyalkyl, substituted amino, carboxamido and the like.

The preferred groups representing $R_2$ in the structure (I), include: hydrogen, chloro, bromo, hydroxy, methoxy, methyl, trifluoromethyl, vinyl, hydroxymethyl, chloromethyl, bromomethyl, azidomethyl, acyloxymethyl, carbamoyloxymethyl, 1,2,3-triazolylmethyl, 1,2,4-triazol-1-yl methyl, imidazol-1-yl methyl, pyrazol-1-yl methyl, thiazolylthiomethyl, isothiazolylthiomethyl, tetrazolylthiomethyl, triazinylthiomethyl, 1-substituted pyridinium-4-ylthiomethyl, 2,3-cyclopenteno-1-substituted pyridinium-4-ylthiomethyl, pyridyl-2-ylthiomethyl, pyridyl-4-ylthiomethyl, 1,3,4-thiadiazolylthiomethyl, 1,2,3-thiadiazolylthiomethyl, 1,2,4-thiadiazolylthiomethyl, 1H-1,2,3-triazolylthiomethyl, 4H-1,3,4-triazolylthiomethyl, 2H-1,2,4-triazolylthiomethyl, s-triazolo[1,5-a]pyrimidinylthiomethyl, 1H-triazolo[4,5-e]pyrimidinylthiomethyl, pyridinium methyl, 2,3-cyclopenteno pyridinium methyl, N-methylpyrrolidium methyl, N-methylpiperidinium methyl.

Preferred substituents on the heterocyclic rings are: methyl, hydroxy, oxo, amino, carboxyl, carboxymethyl, methoxycarbonylmethyl, ethoxycarbonylmethyl, tert-butoxycarbonyl methyl, hydroxymethyl, hydroxyethyl, dimethylaminomethyl.

$R_3$ is hydrogen, $C_{1-6}$ alkoxy, more preferably $R_3$ is methoxy and ethoxy.

In the structural formula (I), n is 0, 1, 2, 3 or 4. More specifically, n is 1, 2, or 3.

The present invention also includes the salts of those compounds of cephem (I). Among the salts of the compound (I), especially pharmaceutically acceptable salts are used when the compound (I) is applied as an anti-elastase agent and other salts are utilized as intermediates for synthesis. Examples of the salts of compound (I) include the inorganic base salts, ammonium salts, organic base salts, basic amino acid salts, inorganic acid addition salts, organic acid addition salts. Inorganic bases that can form the inorganic base salts include alkaline metals (e.g. sodium, potassium) and alkaline earth metals (e.g. calcium, magnesium); organic bases that can form the organic base salts include procaine, 2-phenylethylbenzylamine, dibenzylethylene-diamine, ethanolamine, diethanolamine; inorganic acids that can form the inorganic acid addition salts include hydrochloric acid, hydrobromic acid, phosphoric acid, nitric acid, sulfuric acid; organic acids that can form the organic acid addition salts include p-toluenesulfonic acid, methanesulfonic acid, trifluoroacetic acid, acetic acid, formic acid, oxalic acid, maleic acid, succinic acid; basic amino acids that can form the basic amino acid salts include lysine, arginine, ornithine and histidine. Among these salts, the base salts (i.e. inorganic base salts, ammonium salts, organic base salts and basic amino acid salts) mean base salts which can be formed when an acid group such as carboxyl or sulfo group is present in the structural formula (I). The acid addition salts (i.e. inorganic acid addition salts and organic acid addition salts) mean acid addition salts which can be formed when a basic group, (such as amino, piperazine, guanidino, monoalkylamino, dialkylamino, cycloalkylamino, arylamino, cyclicamino or nitrogen containing heterocyclic group) is present in the structural formula (I).

The present invention also includes those compounds of the structural formula (I) that have suitably pharmaceutically acceptable in vivo hydrolysable esters, namely those esters which hydrolyze in the human body to produce the parent acid or its salt. Examples of such metabolically unstable, non-toxic esters include $C_{1-5}$ alkanoyloxymethyl ester, $C_{1-5}$ alkanoyloxyethyl ester, $C_{1-6}$ alkoxy $C_{1-4}$ alkyl ester or 1-($C_{1-6}$ alkoxycarbonyloxy) $C_{1-6}$ alkyl ester, more specifically acetoxymethyl ester, 1-acetoxyethyl ester, 1-acetoxybutyl ester, 2-acetoxyethyl ester, pivaloyloxy- methyl ester, methoxymethyl ester, ethoxymethyl ester, isopropoxymethyl ester, 1-methoxyethyl ester, 1-ethoxyethyl ester, ethoxycarbonyloxymethyl ester, 1-(ethoxycarbonyl)ethyl ester, tertbutoxycarbonyloxymethyl ester, 1-(tert-butoxycarbonyloxy) ethyl ester, and other such ester groups which have been or can be used in the penicillin and cephalosporin art.

The method for preparing the cephem sulfone (I) of this invention is described in the following process:

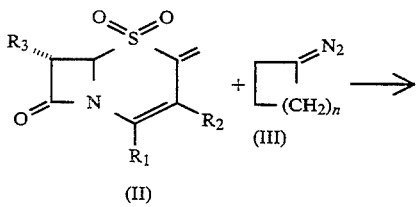

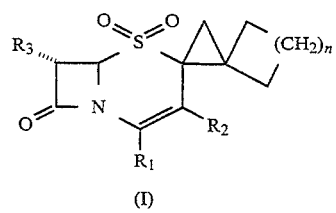

The starting compound (II) can be easily prepared by a known method [e.g. U.S. patent application No. 685,960 (pending), U.S. patent application No. 747,762 (pending), U.S. patent application No. 4,547,371] or one analogous thereto.

The cephem sulfone (I) can be prepared by carrying out a cycloaddition reaction of the compound (II) with a cycloalkyl diazo derivative of the formula (III) wherein the symbols have the same meaning as described before.

The diazo derivative (III) is usually used in an amount of 1 to 5 moles, preferably 1 to 2 moles, per 1 mole of the compound (II) The reaction is conducted at −40° C. to 50° C., preferably at −30° C. to 30° C., and most desirably at −10° C. to 10° C. The reaction time varies depending on the species of the compounds (II) and (III), the kind of solvent (also the mixing ratio, if a mixed solvent is used), the reaction temperature, etc., being usually 1 minute to 10 hours, preferably 15 minutes to 3 hours.

The present invention also includes the following compounds (IV), (V) and (VI) which are obtained from the cycloaddition reaction.

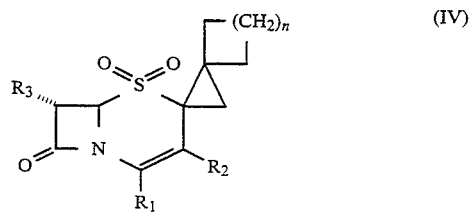

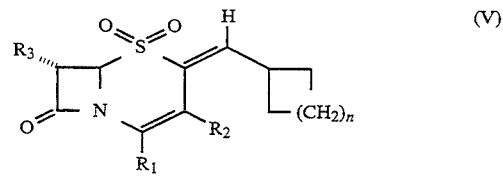

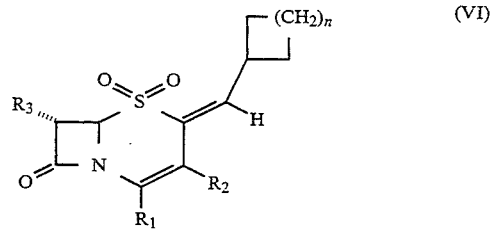

More specifically, the most preferred embodiments of the present invention is comprised of the following compounds; but it should be understood that the present invention is not limited to such specific compounds.

t-Butyl 7 α-methoxy-2-spiro(2'-spirocyclopentyl)cyclopropyl-3-methyl-3-cephem-4-carboxylate-1,1-dioxide;

t-Butyl 7 α-methoxy-2-spiro(2'-spirocyclohexyl)cyclopropyl-3-methyl-3-cephem-4-carboxylate-1,1-dioxide;

7α-Methoxy-2-spiro(2'-spirocyclopentyl)cyclopropyl-3-methyl-3-cephem-4-carboxylic acid -1,1-dioxide, and its sodium salt;

7 α-Methoxy-2-spiro(2'-spirocyclohexyl)cyclopropyl-3-methyl-3-cephem-4-carboxylic acid -1,1-dioxide, and its sodium salt;

7α-Methoxy-2-spiro(2'-spirocyclopentyl)cyclopropyl-3-methyl-3--cephem-4-[{(4-N-methyl)piperazine}carboxamide]-1,1-dioxide, and its hydrochloride salt;

7α-Methoxy-2-spiro(2'-spirocyclopentyl)cyclopropyl-3-methyl-3-cephem-4-[{(4-t-butoxycarbonyl)-piperidine}carboxamide]-1,1-dioxide;

7α-Methoxy-2-spiro(2'-spirocyclopentyl)cyclopropyl-3-methyl-3-cephem-4-[{(4-carboxy)piperidine}carboxamide]-1,1-dioxide, and its sodium salt;

7α-Methoxy-2-spiro(2'-spirocyclopentyl)cyclopropyl-3-methyl-3-cephera-4-[{(4-N-t-butoxycarbonylmethyl)piperazine}carboxamide]-1,1-dioxide;

7α-Methoxy-2-spiro(2α-spirocyclopentyl)cyclopropyl-3 -methyl-3-cephem-4-[{(4-N-acetic acid)-piperazine)carboxamide]-1,1-dioxide, and its sodium salt;

7 α-Methoxy-2-spiro(2'-spirocyclohexyl)cyclopropyl-3-methyl-3- cephen-4-[{(4-N-methyl)piperazine}carboxamide]-1,1-dioxide, and its hydrochloride salt;

7 α-Methoxy-2-spiro(2'-spirocyclohexyl)cyclopropyl-3 -methyl-3-cephem-4-[{(4-N-t-butoxycarbonyl methyl)piperazine)carboxamide]-1,1-dioxide;

7 α-Methoxy-2-spiro(2'-spirocyclohexyl)cyclopropyl-3-methyl-3-cephem-4-[{(4-N-acetic acid)-piperazine}carboxamide]-1,1-dioxide, and its sodium salt;

t-Butyl 7 α-methoxy-2-spiro(2'-spirocyclopentyl)cyclopropyl-3-[(2,5-dihydro-6-hydroxy-2-methyl-5-oxo-1,2,4-triazin-3-yl)thiomethyl]-3 -cephem-4-carboxylate-1,1-dioxide and its sodium salt;

t-Butyl 7 α-methoxy-2-spiro(2'-spirocyclopentyl)cyclopropyl-3-[(1-methyl-1,2,3,4-tetrazole-5-yl)thiomethyl]-3-cephem-4-carboxylate-1,1-dioxide;

t-Butyl 7 α-methoxy-2-spiro(2'-spirocyclopentyl)cyclopropyl-3-[(2-methyl-1,3,4-thiadiazole-5-yl)thiomethyl]-3-cephem-4-carboxylate-1,1-dioxide;

t-Butyl-7 α-methoxy-2-spiro(2'-spirocyclopentyl)cyclopropyl-3-[(pyridyl-4-yl)thiomethyl]-3-cephem-4-carboxylate-1,1-dioxide;

t-Butyl-7 α-methoxy-2-spiro(2'-spirocyclopentyl)cyclopropyl-3-[(pyridyl-2-yl)thiomethyl]-3-cephem-4-carboxylate-1,1-dioxide;

t-Butyl-7 α-methoxy-2-spiro(2'-spirocyclopentyl)cyclopropyl-3-bromomethyl-3-cephem-4-carboxylate-1,1-dioxide;

t-Butyl-7 α-methoxy-2-spiro(2'-spirocyclopentyl)cyclopropyl-3-acetoxymethyl-3-cephem-4-carboxylate-1,1-dioxide;

7 α-Methoxy-2 -spiro(2'-spirocyclopentyl)cyclopropyl-3-[(2,5-dihydro-6-hydroxy-2-methyl-5-oxo-1,2,4-triazin-3-yl)thiomethyl]-3-cephem-4-piperidinecarboxamide-1,1-dioxide, and its sodium salt;

7,7-Dihydro-2-spiro (2'-spirocyclopentyl)cyclopropyl-3-methyl-3-cephera-4-[{(4-carboxy)piperidine}carboxamide]-1,1-dioxide, and its sodium salt;

7,7-Dihydro-2-spiro(2'-spirocyclopentyl)cyclopropyl-3-methyl-3-cephem-4-[(N-methyl-N-acetic acid)-]carboxamide-1,1-dioxide, and its sodium salt;

7 α-Methoxy-2-spiro(2'-spirocyclopentyl)cyclopropyl-3-[(2,5-dihydro-6-hydroxy-2-methyl-5-oxo-1,2,4-triazin-3-yl(thiomethyl]-3-cephera-4-[{(4-carboxy)-piperidine}carboxamide]-1,1-dioxide, and its sodium salt;

7α-Methoxy-2-spiro(2'-spirocyclopentyl)cyclopropyl-3-methyl-3-cephem-4-methylcarbonyl-1,1-dioxide;

7α-Methoxy-2-spiro(2'-spirocyclopentyl)cyclopropyl-3 -methyl-3-cephem-4-[4'-(methyl)-4'-(methoxyimino)]-1,1-dioxide;

7α-Methoxy-2-spiro(2'-spirocyclopentyl)cyclopropyl-3-methyl-3-cephem-4-[{(4-carboxamide)piperidine}carboxamide]-1,1-dioxide;

7α-Methoxy-2-spiro(2'-spirocyclopentyl)cyclopropyl-3-methyl-3-cephem-4-[{(4-cyano)piperidine}carboxamide]-1,1-dioxide;

7α-Methoxy-2-spiro(2'-spirocyclopentyl)cyclopropyl-3-methyl-3-cephem-4-[{(4-hydroxy)piperidine}carboxamide]-1,1-dioxide;

7α-Methoxy-2-spiro(2'-spirocyclopentyl)cyclopropyl-3-methyl-3-cephem-4-[{(4-hydroxyethyl)-piperidine}carboxamide]-1,1-dioxide;

7 α-Methoxy-2-spiro(2'-spirocyclopentyl)cyclopropyl-3-methyl-3-cephera-4-[{(4-bromoethyl)piperidine)-carboxamide]-1,1-dioxide;

7 α-Methoxy-2-spiro(2'-spirocyclopentyl)cyclopropyl-3-methyl-3-cephem-4-[{(4-diethoxyphosphinylethyl)piperidine}-carboxamide]-1,1-dioxide.

BIOLOGICAL EVIDENCE

The in vitro test data on anti-elastase activity of exemplary derivatives having the structural formula I are shown in Table I herebelow:

TABLE I

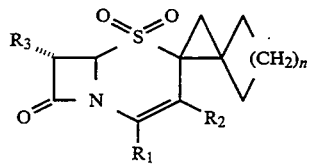

IC50 VALUES OF 2-SPIRO(2'-SPIROCYCLOALKYL)CYCLOPROPYL
CEPHALOSPORIN SULFONES AGAINST HLE

| COMPOUND | $R_1$ | $R_2$ | $R_3$ | n | $IC_{50}$ (nM) |
|---|---|---|---|---|---|
| 1 | $COOBu^t$ | $CH_3$ | $CH_3O$ | 2 | 4.17 |

TABLE I-continued
| | | | | | |
|---|---|---|---|---|---|
| 2 | 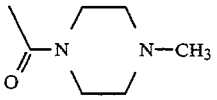 | CH₃ | CH₃O | 2 | 27.3 |
| 3 | 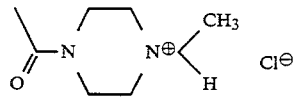 | CH₃ | CH₃O | 2 | 24.4 |
| 4 | 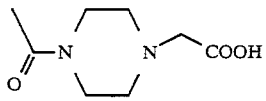 | CH₃ | CH₃O | 2 | 139.0 |
| 5 | 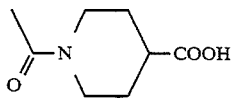 | CH₃ | CH₃O | 2 | 58.1 |
| 6 | COOBu$^t$ | CH₃ | CH₃O | 3 | 3.47 |
| 7 | 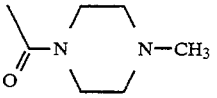 | CH₃ | CH₃O | 3 | 6.40 |
| 8 | 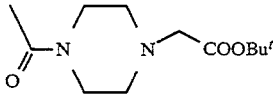 | CH₃ | CH₃O | 3 | 8.37 |
| 9 | 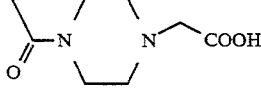 | CH₃ | CH₃O | 3 | 27.0 |
| 10 | 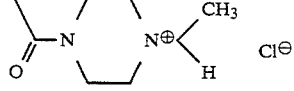 | CH₃ | CH₃O | 3 | 8.4 |
| 11 | COOBu$^t$ | CH₂OAc | CH₃O | 2 | 9.1 |
| 12 | COOBu$^t$ | 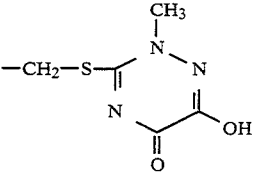 | CH₃O | 2 | 15.0 |
| 13 | COOBu$^t$ | 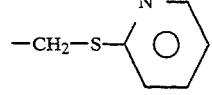 | CH₃O | 2 | 9.4 |
| 14 | COOBu$^t$ | 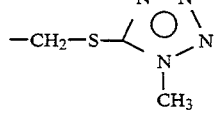 | CH₃O | 2 | 15.3 |
| 15 | COOBu$^t$ | 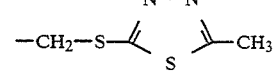 | CH₃O | 2 | 10.3 |

TABLE I-continued

| # | Structure | R | R' | n | Value |
|---|---|---|---|---|---|
| 16 | [piperidine-N-C(=O)CH3] | -CH2-S-C(=N-N(CH3)-N=C(ONa)-C(=O)-) (triazine system) | OCH3 | 2 | 32.4 |
| 17 | [1-acetyl-piperidin-4-yl-COOBu^t] | CH3 | H | 2 | 870 |
| 18 | [CH3-C(=O)-CH3] (acetone-like) | CH3 | OCH3 | 2 | 10.7 |
| 19 | [CH3-C(=N-OCH3)-CH3] | CH3 | OCH3 | 2 | 80.7 |
| 20 | [1-acetyl-piperidin-4-yl-CONH2] | CH3 | OCH3 | 2 | 8.4 |
| 21 | [1-acetyl-phenyl] (acetophenone) | CH3 | OCH3 | 2 | 3.9 |
| 22 | COOCHPh2 | CH3 | H | 2 | 478 |
| 23 | [CH3-C(=O)-N(CH3)-CH2COOH] | CH3 | OCH3 | 2 | 75 |
| 24 | [1-acetyl-piperidin-4-yl-COONa] | -CH2-S-C(=N-N(CH3)-N=C(ONa)-C(=O)-) | OCH3 | 2 | 34 |

ENZYME ASSAY FOR INHIBITION OF HLE

ENZYME: Purified elastase from human white blood cells.
SUBSTRATE: MeO-succinyl-L-alanyl-L-alanyl-L-prolyl-L-valine-p-nitroanilide
REACTION MIXTURE: 10 mM phosphate buffer (pH 7.6)
500 mM NaCl
10% dimethylsulfoxide
0.35 mM substrate The enzyme activity was determined by monitoring the increase in absorbance at 410 nm caused by the hydrolysis of chromogenic substrates. Inhibition of enzyme by the compounds described were determined after a 10 minute preincubation with the enzyme in the reaction mixture minus substrate. Reaction was initiated by the addition of substrate. The concentration of human leukocyte elastase used for assay was at 10 nM.

For therapeutic administration, a compound having the structural formula I, is used in the form of conventional pharmaceutical preparation which contains said compounds as an active ingredient in admixture with a pharmaceutically acceptable carrier such as an organic or inorganic solid or liquid excipient which is suitable for oral, parenteral or external administration. The pharmaceutical preparations may be in solid form such as capsule, tablet, ointment, etc. or in liquid form such as solution, suspension or emulsion. There may be included in the above preparation auxiliary substances, stabilizing agents, wetting or emulsifying agents, buffers and the other commonly used additives.

In general, a daily dose of between 0.2 mg and 150 mg, or even more per kilogram of body weight, per day may be administered to a patient. However, the dose level may vary and will depend upon a variety of factors such as the activity of the specific compound employed, the age, body weight, sex, diet, time of administration, route of administration, etc. The following examples are provided to demonstrate the operability of the present invention.

EXAMPLE 1 t-Butyl 7α-methoxy-2-spiro(2'-spirocyclopentyl)cyclopropyl-3-methyl-3-cephem-4-carboxylate-1,1-dioxide To a suspension of anhydrous magnesium sulfate (3.5 g) in ether (50 ml) cooled to −15° C. was added silver oxide (5.10 g), followed by cyclopentanone hydrazone (2.16 g). A solution of potassium hydroxide in methanol (1 ml) was added dropwise. Within three to five minutes, a deep red color was developed. The reaction mixture was filtered quickly through a small bed of Celite. To the flitrate, a solution of t-butyl 7α-methoxy-2-methylene-3-methyl-3-cephem-4-carboxylate-1,1-dioxide in methylene chloride (100 ml) was added and the reaction mixture was stirred at room temperature for 2 hours. The mixture was filtered through Celite and the filtrate was concentrated to dryness which was purified over a silica gel column using a mixture of hexane-ethyl acetate.

The first eluting component was:
t-Butyl-7α-methoxy-2(Z)-[(cyclopentyl)methylene]-3-methyl-3-cephem-4-carboxylate-1,1-dioxide (1.23 g, 28.1%); $^1$H NMR (CDCl$_3$): δ 6.35 (d, 1H, J=10.7 Hz); (d, 1H, J=1.4 Hz); 4.67 (d, 1H, J=1.4 Hz); 3.68–3.84 (m, 1H); 3.57 (s, 3H); 2.07 (s, 3H); 1.55 (s, 9H); 1.25–1.80 (m, 8H).

The second eluting component was:
t-Butyl-7α-methoxy-2-spiro(3'-spirocyclopentyl) cyclopropyl-3-methyl-3-cephem-4-carboxylate-1,1-dioxide. $^1$H NMR (CDCl$_3$): δ 4.87 (d, 1H, J=1.5 Hz); 4.57 (d, 1H, J=1.5 Hz); 3.55 (s, 2.14 (s, 3H); 1.83 (d, 1H, J=6.4 Hz); 1.62–2.00 (m, 8H); 1.53 (s, 9H); 1.48 (d, 1H. J=6.4 Hz) .

The third eluting component was:
t-Butyl-7α-methoxy-2(E)-[(cyclopentyl)methylene]-3-methyl-3-cephem-4-carboxylate-1,1-dioxide (0.41 g, 8.88%) . $^1$H NMR (CDCl$_3$): δ 6.73 (d, 1H, J=10.8 Hz); 4.96 (d, 1H, J=1.6 Hz); 4.63 (d, 1H,. J=1.6 Hz); 3.48 (s, 3H); 2.75–2.88 (m, 1H); 2.23 (s, 3H); 1.48 (s, 9H); 1.18–2.07 (m, 8H).

The fourth eluting component was:
t-Butyl-7α-methoxy-2-spiro(2'-spirocyclopentyl)cyclopropyl-3-methyl-3-cephem-4-carboxylate-1,1-dioxide(1.65 g, 37.67%). $^1$H NMR (CDCl$_3$): δ 5.10 (d, 1H, J=1.8 Hz); 4.57 (d, 1H, J=1.8 Hz); 3.56 (s, 3H); 1.95 (d, 1H, J=6.5 Hz); 1.76 (s, 3H); 1.56 (s, 9H); 1.60–1.96 (m, 9H).

EXAMPLE 2 t-Butyl-7α-methoxy-2-spiro(2'-spirocyclopentyl)cyclopropyl--3-[(1-methyl-1,2,3,4-tetrazole-5-yl)thiomethyl]-3-cephem-4-carboxylate-1,1-dioxide Step A:
To a solution of t-butyl-7α-methoxy-2-spiro(2'-spirocyclopentyl)cyclopropyl-3-methyl-3-cephem-4-carboxylate-1,1-dioxide (Example 1, 761 mg, 1.9146 mmols) in carbon tetrachloride (35 ml) was added N-bromosuccinimide (374.8 rag, 2.1060 mmol) followed by AIBN (15.7 mg, 0.0957 mmols). The mixture was heated to reflux at 90° C. for 21 hours; cooled to 0° C., the precipitated solid was removed by filtration. The filtrate was concentrated under reduced pressure to give a crude mass (1.15 g) which was chromatographed over a silica gel column using methylene chloride as eluant to give 670 mg (73.5%) of t-butyl-7α(-methoxy-2-spiro (2'-spirocyclopentyl) cyclopropyl-3-bromomethyl-3-cephem-4-carboxylate-1,1-dioxide. $^1$H NMR (CDCl$_3$): δ 5.14 (d, 1H, J=2.0 Hz); 4.60 (d, 1H, J=2.0 Hz); 4.35 (d, $^1$H, J=10.8 Hz); 3.57 (s, 3H); 3.32 (d, 1H, J=10.8 Hz); 2.16 (d, 1H, J=7.2 Hz); 1.65 (d, 1H, J=7.2 Hz); 1.60 (s, 9H); 1.55–2.00 (m, 8H).

Stem B:
To a solution of t-butyl-7α-methoxy-2-spiro(2'-sprioocyclopentyl)cyclopropyl-3-bromomethyl-3-cephem-4-carboxylate- 1,1-dioxide (Example 2, step A; 100 mg, 0.2099 mmol) in acetonitrile (2 ml) was added 1-methyl-5-mercapto-1,2,3,4-tetrazole (24.38 mg, 0.2099 mmol) followed by triethylamine (64 μl, 0.4618 mmol). After stirring at room temperature for 1 hour, the solvent was removed under reduced pressure and the residue was dissolved in methylene chloride; washed with dilute hydrochloric acid, followed by dilute sodium bicarbonate solution, dried over anhydrous sodium sulfate and concentrated to give a brown foam which was purified over a silica gel column using hexane-ethyl acetate mixture as eluant to give the title compound as a yellow foam (81 mg, 76%). $^1$H NMR (CDCl$_3$): δ 5.12 (d, 1H, J=1.9 Hz); 4.60 (d, 1H, J=1.9 Hz); 4.26 (d, 1H, J=13.0 Hz); 3.92 (s, 3H); 3.80 (d, 1H, J=13.0 Hz); 3.58 (s, 3H); 1.72–1.97 (m, 10H); 1.59 (s, 9H).

EXAMPLE 3 t-Butyl-7α-methoxy-2-spiro(2'-spirocyclopentyl)cyclopropyl-3-[(2-methyl-1,3,4-thiadiazole-5-yl)thiomethyl]-3-cephem-4-carboxylate-1,1-dioxide To a solution of t-butyl-7α-methoxy-2-spiro(2'-spirocyclopentyl) cyclopropyl-3-bromomethyl-3-cephem-4-carboxylate-1,1-dioxide (Example 2, Step A; 100 mg, 0.2099 mmol) in acetonitrile (2 ml) was added 5-methyl-2-mercapto-1,3,4-thiadiazole (27.7 mg, 0.2099 mmol), followed by triethylamine (64 μL, 0.4618 mmol). After stirring at room temperature for 4 hours, the solvent was removed under reduced pressure and the residue was dissolved in methylene chloride, washed with dilute hydrochloric acid, dilute sodium bicarbonate solution, water and brine, dried over anhydrous sodium sulfate and concentrated to give a brown foam which was purified over a silica gel column using hexane-ethyl acetate mixture as eluant to give 54 mg (50%) of the title compound as a light yellow foam. $^1$H NMR (CDCl$_3$): δ 5.12 (d, 1H, J=1.9 Hz); 4.59 (d, 1H, J=1.9 Hz); 4.20 (d, 1H, J=13.0 Hz); 3.96 (d, 1H, J=13.0 Hz); 3.57 (s, 3H); 2.72 (s, 3H); 1.94 (d, 1H, J=9.3 Hz); 1.73–1.96 (m, 9H); 1.58 (s, 9H).

EXAMPLE 4 t-Butyl-7α-methoxy-2-spiro(2'-spirocyclopentyl)cyclopropyl-3-[(pyridyl-2-yl)thiomethyl]-3-cephem-4-carboxylate-1,1-dioxide To a solution of t-butyl-7α-methoxy-2-spiro(2'-spirocyclopentyl) cyclopropyl-3-bromomethyl-3-cephem-4-carboxylate-1,1dioxide (Example 2, Step A; 100 mg, 0.2099 mmol) in acetonitrile (2 ml) were added 2-mercapto pyridine (23.6 mg, 0.2099 mmol) and triethylamine (64 μL, 0.4618 mmol). The reaction was worked up in the same manner as described in Example 3. The title compound was obtained as a white foam (54 rag, 51%). ¹H NMR (CDCl₃): δ 8.37–8.39 (m, 1H); 7.44–7.52 (m, 1H); 7.16–7.20 (m, 1H); 6.95–7.02 (m, 1H); 5.12 (d, 1H, J=1.9 Hz); 4.58 (d, 1H, J=1.9 Hz); 3.93 (ABq, 2H, J=13.25 and 22.15 Hz); 3.57 (s, 3H); 1.64–1.96 (m, 10H); 1.57 (s, 9H).

EXAMPLE 5 t-Butyl-7α-methoxy-2-spiro(2'-spirocyclopentyl)cyclopropyl-3[(pyridyl-4-yl)thiomethyl]-3-cephem-4-carboxylate-1,1-dioxide The reaction was done in the same manner as described in Example 4 by using 4-mercapto pyridine. The yield of the title compound was 60 mg (57.7%). ¹H NMR (CDCl₃): δ 8.42 (d, br, 2H); 7.14 (d, br, 2H); 5.14 (d, 1H, J=2.0 Hz); 4.61 (d, 1H, J=2.0 Hz); 4.15 (d, 1H, J=11.7 Hz); 3.58 (s, 3H); 2.93 (d, 1H, J=11.4 Hz); 2.075 (d, 1H, J=7.3 Hz); 1.56–2.06 (m, 8H); 1.536 (s, 9H); 1.43 (d, 1H, J=7.3 Hz).

EXAMPLE 6 t-Butyl-7α-methoxy-2-spiro(2'-spirocyclopentyl)cyclopropyl-3-[(2,5-dihydro-6-hydroxy-2-methyl-5-oxo-1,2,4-triazin-3-yl)-thiomethyl]-3-cephem-4-carboxylate-1,1-dioxide Step A:

To a solution of t-butyl-7α(-methoxy-2-spiro (2'-spirocyclopentyl)cyclopropyl-3-bromomethyl-3-cephem-4-carboxylate-1,1-dioxide (Example 2, Step A; 200 mg, 0.4198 mmol) in acetonitrile (5 ml) were added 2,5-dihydro-6-diphenylmethyloxy-2-methyl-3-mercapto-5-oxo-1,2,4-triazine (137 mg, 0.4198 mmol) and triethylamine (0.8396 mmol). The reaction mixture was stirred at room temperature overnight, diluted with ethyl acetate, washed with dilute hydrochloric acid, sodium bicarbonate solution, water and brine, dried over anhydrous Na₂SO₄, filtered and concentrated to give a light brown foam. The product was purified over a silica gel column using hexane-ethyl acetate mixture as eluant. The yield of the title compound was 170 mg (56.3%). ¹H NMR (CDCl₃): δ 7.30–7.46 (m, 10H); 6.75 (s, 1H); 5.09 (d, 1H, J=2.0 Hz); 4.58 (d, 1H, J=2.0 Hz); 3.9 (ABq, 2H, J=13.2 and 23.0 Hz); 3.62 (s, 3H); 3.56 (s, 3H); 1.61–1.96 (m, 10H); 1.56 (s, 9H).

Step B:

To a stirred solution of t-butyl-7α-methoxy-2-spiro (2'-spirocyclopentyl)cyclopropyl-3-[(2,5-dihydro-6-hydroxy-2-methyl-5-oxo-1,2,4-triazin-3-yl)thiomethyl]-3-cephem-4-carboxylate-1,1-dioxide (from Step A, 146 mg, 0.2196 mmol) in dry methylene chloride (5 ml) was added trifluoroacetic acid (204 μL, 1.2 mmol). The mixture was stirred at room temperature for 2.5 hours. The solvent was removed under reduced pressure and the residue was diluted with ether and treated with hexane. The precipitated white solid was collected by filtration, 81 mg (75%). ¹H NMR (CDCl₃): δ 5.11 (d, 1H, J=1.9 Hz); 4.59 (d, 1H, J=1.9 Hz); 4.30 (s, br, 1H); 3.79 (ABq, 2H, J=13.2 Hz, J₂=28.3 Hz); 3.75 (s, 3H); 3.58 (s, 3H); 1.99 (d, 1H, J=7.0 Hz); 1.73–2.00 (m, 9H); 1.58 (s, 9H).

EXAMPLE 7

7α-Methoxy-2-spiro (2'-spirocyclopentyl)cyclopropyl-3-methyl-3-cephem-4-[{(4-carboxy)piperidine}carboxamide]-1,1-dioxide Step A:

A solution of t-butyl-7α-methoxy-2-spiro(2'-spirocyclopentyl)-cyclopropyl-3-methyl-3-cephem-4-carboxylate-1,1-dioxide (Example 2, 0.50 g, 1.26 mmol) in formic acid (10 ml) was stirred at 50° C. for a period of 1 hour and the formic acid was removed by freeze-drying. The residue was washed several times with a mixture of hexane-ether (9.5:0.5) and finally dissolved in methylene chloride. Evaporation of the solvent in vacuo gave a foam (0.408 g, 95%).

¹H NMR (CDCl₃): δ 8.03 (s, br, 1H); 5.13 (d, 1H, J=1.6 Hz); 4.62 (d, 1H, J=1.6 Hz); 3.58 (s, 3H); 2.046 (d, 1H, J=6.6 Hz); 1.67 (d, 1H, J=6.6 Hz); 1.56–2.00 (m, 8H); 1.91 (s, 3H).

STEP B:

To a stirred and ice-cooled solution of 7α-methoxy-2-spiro(2'-spirocyclopentyl)cyclopropyl-3-methyl-3-cephem-4-carboxylic acid-1,1-dioxide (from Step A, 2.96 g, 8.7 mmol) in dry methylene chloride (100 ml) under nitrogen was added oxalyl chloride (1.46 g, 1.13 mmol) followed by four drops of dimethylformamide. The reaction mixture was stirred for 15 min. at 10° C. and at room temperature for 50 min. Volatile materials were removed under reduced pressure. The solid obtained was dissolved in dry methylene chloride (100 ml). To this solution, a solution of 4-t-butoxycarbonyl piperidine (1.61 g, 8.7 mmol) in methylene chloride (5 ml) was added, followed by triethylamine (0.934 g, 9.1 mmol). The reaction mixture was stirred at room temperature for 1.5 hr, then diluted with 100 ml of methylene chloride. The methylene chloride solution was washed successively with sodium bicarbonate solution, brine and dried over anhydrous sodium sulfate. Evaporation of the solvent gave a light brown solid which was purified over a silica gel column using hexane-ethyl acetate mixture (3:2) as eluant. The title compound was obtained as a white solid (3.33 g, 75.5%). ¹H NMR (CDCl₃): δ 5.11–5.14 (m, 1H); 4.58–4.59 (m, 1H); 4.31–4.50 (m, 1H); 3.65–3.85 (m, 1H); 3.54 and 3.55 (2s, 3H); 2.90–3.20 (m, 2H); 2.35–2.55 (m, 1H); 1.50–2.04 (m, 14H); 1.58 (s, 3H); 1.45 (s, 9H).

Step C:

A solution of 7α-methoxy-2-spiro(2'-spirocyclopentyl)cyclopropyl-3-methyl-3-cephem-4- [{(4-t-butoxycarbonyl)piperidine}carboxamide]-1,1-dioxide (3.2 g, 6.3 mmol) in anhydrous formic acid (200 ml) was stirred under nitrogen at 40°–45° C. over a period of 1.5 hours and formic acid was removed by freeze-drying. The residual mass was digested with a mixture of hexane-ether (8.5:1.5); the precipitated solid was filtered off, 2.45 g (85.8%). ¹H NMR (CDCl₃): δ 5.13–5.15 (m, 1H); 4.60–4.61 (m, 1H); 4.25–4.55 (m, 1H); 3.5–3.90 (m, 1H); 3.54 (s, 3H); 2.90–3.25 (m, 2H); 2.50–2.75 (m, 1H); 1.51–2.10 (m, 14H); t153 and 1.58 (2s, 3H).

EXAMPLE 8

7α-Methoxy-2-spiro(2'-spirocyclopentyl)cyclopropyl-3-methyl-3-cephem-4-[{(4-N-methyl)piperazine}carboxamide]-1,1-dioxide hydrochloride Step A:

To a stirred and ice-cooled solution of 7α-methoxy-2-spiro(2'-spirocyclopentyl)cyclopropyl-3-methyl-3-cephem-4-carboxylic acid-1,1-dioxide (Example 7, Step A; 2.75 g, 8.06 mmol) in dry methylene chloride (100 ml) under nitrogen was added oxalyl chloride (1.36 g, 10.5 mmol) followed by three drops of DMF. The reaction mixture was stirred at 10° C. for 15 min and then at room temperature for 50 min. The volatile solvents were removed under reduced pressure. The solid thus obtained was dissolved in 80 ml of dry methylene chloride and stirred under nitrogen. To the above solution was added a solution of N-methylpiperazine (0.824 g, 8.06 mmol) followed by triethylamine (0.865 g, 8.46 mmol). The reaction mixture was stirred at room temperature for one hour, then diluted with methylene chloride (100 ml); washed successively with sodium bicarbonate solution, brine, dried ($Na_2SO_4$) and concentrated to give a light yellow foam. The product was purified over a silica gel column using ethyl acetate-methanol (9.5:0.5) as eluant; yield 1.96 g (57.5%). $^1$H NMR ($CDCl_3$): δ 5.12 (d, 1H, J=1.9 Hz); 4.60 (d, 1H, J=1.9 Hz); 3.55 (s, 3H); 3.5–4.0 (m, 4H); 2.33–2.50 (m, 4H); 2.33 (s, 3H); 1.92 (d, 1H, J=6.4 Hz); 1.56–1.93 (m, 8H); 1.55 (s, 3H); 1.52 (d, 1H, J=6.4 Hz).

STEP B:

1.96 g (4.63 mmol) of 7α-methoxy-2-spiro(2'-spirocyclopentyl)cyclopropyl-3-methyl-3-cephem-4-[{(4-N-methyl)piperazine}carboxamide]-1,1-dioxide (from the previous step) was dissolved in dry methylene chloride (15 ml). A stream of dry hydrogen chloride gas was bubbled through this solution and the reaction mixture was stirred at room temperature for 10 min. The reaction mixture was diluted with 50 ml of anhydrous ether. The precipitated white solid was collected by filtration, 1.9 g (89.2%). $^1$H NMR ($CDCl_3$): δ 5.09 (d, 1H, J=1.7 Hz); 4.76–4.83 (m, 1H); 4.62 (d, 1H, J=1.7 Hz); 3.30–4.20 (m, 5H); 3.56 (s, 3H); 2.90–3.10 (m, 2H); 2.81 (d, 3H, J=4.06 Hz); 1.96 (d, 1H, J=6.5 Hz); 1.55–1.98 (m, 9H); 1.55 (s, 3H).

EXAMPLE 9

7α-Methoxy-2- spiro(2'- spirocyclopentyl)cyclopropyl-3-methyl-3-cephem-4-[{(4-N-acetic acid)-piperazine}carboxamide-1,1-dioxide

STEP A:

To a stirred and ice-cooled solution of 7α-methoxy-2-spiro(2'-spirocyclopentyl)cyclopropyl-3-methyl-3-cephem-4-carboxylic acid-1,1-dioxide (Example 7, Step A; 2.93 g, 8.6 mmol) in dry methylene chloride (100 ml) under nitrogen was added oxalyl chloride (1.45 g, 11.2 mmol) followed by 4 drops of DMF. The reaction mixture was stirred at 10° C. for 15 min and at room temperature for 45 min. The volatile materials were removed under reduced pressure. The residual light yellow foam was dissolved in methylene chloride and stirred under nitrogen. To this reaction mixture was added 4-(t-butoxycarbonyl methyl) piperazine (1.72 g, 8.6 mmol) dissolved in methylene chloride (2 ml), followed by triethylamine (0.923 g, 9.03 mmol). The reaction mixture was stirred at room temperature for one hour and diluted with methylene chloride (100 ml). The organic layer was washed with sodium bicarbonate solution, brine, dried ($Na_2SO_4$) and concentrated under reduced pressure to give a light yellow foam. Purification of the product over a silica gel column using hexane-ethyl acetate mixture as eluant gave the pure compound (3.3 g, 73.5%). $^1$H NMR ($CDCl_3$): δ 5.09 (d, 1H, J=2.0 Hz); 4.56 (d, 1H, J=2.0 Hz); 3.80–4.00 (m, 1H); 3.51 (s, 3H); 3.4–3.7 (m, 3H); 3.12 (s, 2H); 2.56–2.70 (m, 4H); 2.26–2.40 (m, 1H); 1.62–1.98 (m, 10H); 1.52 (s, 3H); 1.43 (s, 9H).

STEP B:

7α(-Methoxy-2-spiro(2'-spirocyclopentyl)cyclopropyl-3-methyl-3-cephem-4-[{(4-N-t-butoxycarbonylmethyl)piperazine}carboxamide]-1,1-dioxide (from Step A; 3.2 g, 6.1 mmol) was dissolved in anhydrous formic acid (150 ml) and the reaction mixture was stirred at 40°–45° C. for 2 hours. Formic acid was removed by freeze-drying. The residual gummy mass was digested with a mixture of hexane-ether (9:1). The precipitated solid was collected by filtration (2.06 g, 72%). $^1$H NMR ($CDCl_3$): δ 5.4–5.5 (br, 1H); 5.11 (d, 1H, J=2.0 Hz); 4.60 (d, 1H, J=2.0 Hz); 4.1–4.2 (m, 1H); 3.5–3.75 (m, 3H); 3.55 (s, 3H); 3.32 (s, br, 2H); 2.70–3.05 (m, 4H); 1.52–1.95 (m, 10H); 1.56 (s, 3H).

EXAMPLE 10 t-Butyl-7α-methoxy-2-spiro(2'-spirocyclohexyl)cyclopropyl-3-methyl-3-cephem-4-carboxylate-1,1-dioxide To a suspension of anhydrous magnesium sulfate (4.0 g) in dry ether (90 ml) cooled to −15° C. was added silver oxide (8.11 g) followed by cyclohexanone hydrazone (3.75 g, 33.4 mmol). A solution of potassium hydroxide in methanol (1 ml) was added dropwise. After stirring at this temperature for three minutes, a deep red color was formed. The reaction mixture was filtered rapidly through a small bed of Celite. To the filtrate a solution of t-butyl-7α-methoxy-2-methylene-3-methyl-3-cephem-4-carboxylate-1,1-dioxide (2.20 g, 6.7 mmol) in methylene chloride (50 ml) was added slowly. The reaction mixture was stirred at room temperature for 2 hours, concentrated under reduced pressure and the crude mass was purified over a silica gel column using hexane-ethyl acetate mixture (6:3) as eluant to give the pure compound (1.1 g, 40%). $^1$H NMR ($CDCl_3$): δ 5.05 (d, 1H, J=2.0 Hz); 4.63 (d, 1H, J=2.0 Hz); 3.56 (s, 3H); 1.92 (s, 3H); 1.55 (s, 9H); 1.23–2.40 (m, 12H).

EXAMPLE 11

7α-Methoxy-2-spiro(2'-spirocyclohexyl)cyclopropyl-3-methyl-3-cephem-4-[{(4-N-methyl)piperazine}carboxamide]-1,1-dioxide

STEP A:

t-Butyl-7α-methoxy-2-spiro(2'-spirocyclohexyl)cyclopropyl-3-methyl-3-cephem-4-carboxylate-1,1-dioxide (Example 10, 2,133 g, 5.18 mmol) was dissolved in anhydrous formic acid (40 ml) and the reaction mixture was stirred at 50° C. for one hour. Formic acid was removed by freeze-drying. The residue thus obtained was digested with hexane; hexane layer was decanted off. This process was repeated several times and the residue was pumped out to give a foam (1.67 g, 91%). $^1$H NMR ($CDCl_3$): δ 5.07 (d, 1H, J=2.0 Hz); 4.65 (d, 1H, J=2.0 Hz); 3.57 (s, 3H); 2.08 (s, 3H); 1.87 (d, 1H, J=6.4 Hz); 1.10–1.90 (m, 11H).

STEP B:

To a stirred and ice-cooled solution of 7α-methoxy-2-spiro(2'-spirocyclohexyl)cyclopropyl-3-methyl-3-cephem-4carboxylic acid-1,1-dioxide (from the previous step; 0.2 g, 0.62 mmol) in dry methylene chloride (5 ml) under nitrogen was added oxalyl chloride (0.092 g, 0.71 mmol), followed by 2 drops of DMF. The reaction mixture was stirred at room temperature for 50 min. The volatile materials were removed under reduced pressure. The residual light yellow foam was dissolved in methylene chloride (10 ml) and stirred under nitrogen at 0° C. To this solution, N-methylpiperazine (0.124 g, 1.24 mmol) was added. The reaction mixture was stirred at ice-temperature for 30 min. and at room temperature for 30 min., diluted with 30 ml of methylene chloride. The methylene chloride layer was washed with water, brine, dried ($Na_2SO_4$) and concentrated under reduced pressure to give a crude product which was purified over a silica gel column using ethyl acetate-methanol mixture as the eluant (0.163 g, 60%). $^1$H NMR (CDCl$_3$): δ 5.08 (d, 1H, J=2.0 Hz); 4.73 (d, 1H, J=2.0 Hz); 3.54 (s, 3H); 3.40–3.90 (m, 4H); 2.35–2.50 (m, 4H); 2.31 (s, 3H); 1.80 (d, 1H, J=6.6 Hz); 1.64 (s, 3H); 1.50 (d, 1H, J=6.6 Hz); 1.17–1.89 (m, 10H).

EXAMPLE 12 t-Butyl-7α-methoxy-2-spiro(2'-spirocyclopentyl)cyclopropyl-3 -acetoxymethyl-3-cephem-4-carboxylate-1,1-dioxide By using the same procedure as described in Example 1, but using t-butyl 7α-methoxy-2-methylene-3-acetoxymethyl-3-cephem-4-carboxylate-1,1-dioxide, the title compound was prepared. $^1$H NMR (CDCl$_3$): δ 5.13 (d, 1H, J=2.0 Hz); 4.60 (d, 1H, J=12.7 Hz); 4.60 (d, 1H, J=2.0 Hz); 4.27 (d, 1H, J=12.7 Hz); 3.57 (s, 3H); 2.08 (s, 3H); 2.01 (d, 1H, J=6.9 Hz); 1.55 (s, 9H); 1.50–1.99 (m, 9H).

EXAMPLE 13

7α-Methoxy-2-spiro (2'-spirocyclopentyl)cyclopropyl-3-[(2,5-dihydro-6-hydroxy-2-methyl-5-oxo-1,2,4-triazin-3-yl) thiomethyl]-3-cephem-4-piperidine carboxamide-1,1-dioxide Step A:

To a stirred and ice-cooled solution of 7α-methoxy-2-spiro(2'-spirocyclopentyl) cyclopropyl-3-methyl-3-cephem-4-carboxylic acid -1,1-dioxide (Example 7, Step A; 3.0 g, 8.8 mmol) in dry methylene chloride (60 ml) under nitrogen was added oxalyl chloride (1.45 g, 11.43 mmol) followed by three drops of DMF. The reaction mixture was stirred at 10° C. for 15 min. and then at room temperature for 45 min. The volatile solvents were removed under reduced pressure. The resulting solid thus obtained was dissolved in methylene chloride. To this solution, a solution of piperidine (1.65 g, 19.4 mmol) in methylene chloride (2 ml) was added and the mixture was allowed to stir for 1 hour at room temperature. The reaction mixture was then diluted with methylene chloride and washed with water followed by brine, dried over anhydrous sodium sulphate. Evaporation of the solvent in vacuo gave a yellow foam, which was purified over a silica gel column. Gradient elution of the column with a mixture of hexane-ethyl acetate gave pure 7α-methoxy-2-spiro(2'-spirocyclopentyl)cyclopropyl-3-methyl-3 -cephem-4 -piperidine carboxamide-1,1-dioxide, as a white foam (2.5 g, 69.4%). $^1$H NMR (CDCl$_3$): δ 5.12 (d, 1H, J=2.0 Hz); 4.60 (d, 1H, J=2.0 Hz); 3.62–3.72 (m, 2H); 3.55 (s, 3H); 3.37–3.45 (m, 2H); 1.92 (d, 1H, J=6.4 Hz); 1.58–1.84 (m, 14H); 1.56 (s, 3H); 1.51 (d, 1H, J=6.4 Hz).

Step B:

To a solution of 7α-methoxy-2-spiro(2'-spirocyclopentyl)-cyclopropyl-3-methyl-3-cephem-4 -piperidine carboxamide-1,1-dioxide (2.41 g, 5.9 mmol) in anhydrous carbon tetrachloride (60 ml) was added N-bromosuccinimide (1.16 g, 6.5 mmol) followed by azoisobutyronitrile (0.097 g, 0.59 mmol). The reaction mixture was refluxed at 80° C. for 24 hr., cooled to room temperature and filtered through Celite. The filtrate was evaporated in vacuo to give a crude mass which was purified over a silica gel column. Gradient elution of the column with a mixture of hexane-ethyl acetate gave the pure product, 7α-methoxy-2-spiro(2'-spirocyclopentyl)cyclopropyl-3-bromomethyl-3-cephem-4-piperidine carboxamide-1,1-dioxide (1.31 g, 45.5%). $^1$H NMR (CDCl$_3$): δ 5.16 (d, 1H, J=2.2 Hz); 4.62 (d, 1H, J=2.0 Hz); 4.06 (d, 1H, J=11.6 Hz); 3.78–3.90 (m, 1H); 3.56 (s, 3H); 3.56–3.65 (m, 2H); 3.43 (d, 1H, J=11.6 Hz); 3.32-3.35 (m, 1H); 2.14 (d, 1H, J=7.1 Hz); 1.65 (d, 1H, J=7.1 Hz); 1.56–2.00 (m, 14H).

Step C:

To a solution of 7α-methoxy-2-spiro(2'-spirocyclopentyl)-cyclopropyl-3-bromomethyl-3-cephem-4-piperidine carboxamide-1,1-dioxide (Example 13, Step B, 0.5 g, 1.03 mmol) in acetonitrile (15 ml) was added 2-methyl-3-mercapto-5-oxo-6-diphenylmethoxy-1,2,4-triazine (0.67 g, 2.05 mmol) followed by triethylamine (0.228 g, 2.3 mmol). The reaction mixture was stirred at room temperature for 16 hr. and acetonitrile was evaporated in vacuo. The crude product was purified over a silica gel column using hexane-ethyl acetate mixture as eluant. The mass of the pure product was 0.417 g (56%). $^1$H NMR (CDCl$_3$): δ 7.26–7.46 (m, 10H); 6.75 (s, 1H); 5.14 (br, s, 1H); 4.62 (d, 1H, J=2.0 Hz); 3.61 (s, 3H); 3.56 (s, 3H); 3.56–3.90 (m, 4H); 3.24–3.47 (br, m, 2H); 1.58–2.05 (m, 16H).

Step D:

To a stirred and ice-cooled solution of 7α-methoxy-2-spiro(2'-spirocyclopentyl)cyclopropyl-3-[(2,5-dihydro-6-diphenylmethoxy-2-methyl-5-oxo-1,2,4 -triazin-3-yl)thiomethyl]-3-cephem-4-piperidine carboxamide-1,1-dioxide (Example 13,. Step C, 377 mg, 0.52 mmol) in anhydrous methylene chloride (4.5 ml) was added dry anisole (8.5 ml) followed by trifluoroacetic acid (13 ml). The reaction mixture was stirred at 0° C. for 1 hr. and evaporated in. vacuo. The gummy residue was digested with a mixture of hexane-ether (2:1). The precipitated solid was dissolved in methylene chloride and evaporated in vacuo to give pure compound, 7α(methoxy-2-spiro (2'-spirocyclopentyl)cyclopropyl-3-[(2,5-dihydro-6-hydroxy-2-methyl-5-oxo-1,2,4-triazin-3-yl)thiomethyl]-3-cephem-4-piperidine carboxamide-1,1-dioxide, as a foam (260 mg, 89%). $^1$H NMR (CDCl$_3$): δ 5.15 (d, 1H, J=2.0 Hz); 4.64 (d, 1H, J=2.0 Hz); 3.74 (s, 3H); 3.57 (s, 3H); 3.57–3.85 (m, 4H); 3.37–3.47 (br, m, H); 1.98 (d, 1H, J=6.8 Hz); 1.50–2.00 (m, 15H).

EXAMPLE 14

7,7-Dihydro-2-spiro(2'-spirocyclopentyl)cyclopropyl-3-methyl-3-cephem-4-[{(4-carboxy)piperidine}carboxamide]1,1-dioxide Step A:

To a suspension of anhydrous sodium sulphate (40 g) in ether (200 ml) cooled to −10° C. was added silver oxide (12.45 g) , followed by cyclopentanone hydrazone (5.28 g, 53.7 mmol). A solution of potassium hydroxide in methanol (2 ml) was added dropwise. Within 5 minutes a deep red color was developed. The reaction mixture was filtered quickly through a small bed of Celite. To the filtrate, a solution of benzhydryl 7,7-dihydro-2-methylene-3-methyl-3-cephem-4-carboxylate-1,1-dioxide (11 g, 26.9 mmol), dissolved in a mixture of methylene chloride and ethyl acetate was added. The mixture was stirred at room temperature for 1 hr. Evaporation of the solvent under reduced pressure gave a white solid which, upon purification by silica gel column chromatography using a mixture of hexane-ethyl acetate as eluant, gave benzhydryl 7,7-dihydro-2-spiro(2'-spirocyclopentyl)-cyclopropyl- 3-methyl-3-cephem-4-carboxylate-1, 1-dioxide (4.60 g, 35.1%). $^1$H NMR (CDCl$_3$): δ 7.26–7.38 (m, 10H); 6.99 (s, 1H); 4.65 (dd, 1H, J=2.4 and 4.9 Hz); 3.60 (dd, 1H, J=2.0 and 15.0 Hz); 3.42 (dd, 1H, J=4.0 and 15.0 Hz); 1.71 (s, 3H); 1.95 (d, 1H, J=6.6 Hz); 1.60 (d, 1H, J=6.6 Hz); 1.54–1.96 (m, 8H).

Step B:

A mixture of benzhydryl 7, 7-dihydro-2-spiro (2'-spirocyclopentyl) cyclopropyl-3-methyl-3-cephem-4-carboxylate-1,1-dioxide (3.0 g, 6.3 mmol) in methylene chloride (25 ml), anhydrous anisole (50 ml) and trifluoroacetic acid (75 ml) was stirred under nitrogen atmosphere at 0° C. for 1 hr. The reaction mixture was concentrated under reduced pressure and the residue was digested with hexane. The precipitated solid was filtered off, washed with hexane and air dried to give a white solid (1.89 g, 96.4%). $^1$H NMR (CDCl$_3$): δ 6.45 (br, s, 1H); 4.70 (br, s, 1H); 3.44–3.55 (m, 2H); 1.91 (s, 3H); 1.67–2.00 (m, 10H).

Step C:

To a stirred and ice-cooled solution of 7,7-dihydro-2-spiro(2'-spirocyclopentyl)cyclopropyl-3-methyl-3-cephem-4-carboxylate-1,1-dioxide (Example 14, Step B, 1.29 g, 4.14 mmol) in anhydrous methylene chloride (25 ml) under nitrogen was added oxalyl chloride (0.684 g, 5.4 mmol) followed by two drops of DMF. The reaction mixture was stirred at room temperature for 1 hr. The volatile materials were removed under reduced pressure. The residue was dissolved in anhydrous methylene chloride and stirred under nitrogen. To this solution, a solution of 4-tert-butoxycarbonyl piperidine (0.768 g, 4.14 mmol) in methylene chloride (1 ml) was added in one portion followed by triethyl amine (0.44 g, 4.4 mmol). The reaction mixture was allowed to stir at room temperature for 1 hr., diluted with methylene chloride, washed successively with water, sodium bicarbonate solution and brine. The organic layer was dried over anhydrous sodium sulphate, evaporated in vacuo to give the crude product which was purified by silica gel column chromatography using a mixture of hexane-ethyl acetate (1:4) as eluant. The pure compound, 7,7-dihydro-2-spiro (2'-spirocyclopentyl) cyclopropyl-3-methyl-3-cephem-4-[{(4-t-butoxycarbonyl)-piperidine}carboxamide]1,1-dioxide was obtained as a foam (1.14 g, 60%). $^1$H NMR (CDCl$_3$): δ 4.66 (dd, 1H, J=2.4 and 4.6 Hz); 4.28–4.53 (m, 1H); 3.75–3.97 (m, 1H); 3.53–3.67 (m, 1H); 3.37 (dd, 1H, J=5.0 and 16.2 Hz); 2.87–3.25 (m, 2H); 2.35–2.55 (m, 1H); 1.53 and 1.59 (2s, 3H); 1.50–2.10 (m, 14H); 1.45 (s, 9H).

Step D:

A mixture of 7,7-dihydro-2-spiro(2'-spirocyclopentyl)cyclopropyl-3-methyl-3-cephem-4-[{(4-tert-butoxycarbonyl) piperidine}carboxamide]-1,1-dioxide (Example 14, Step C, 0.4 g, 0.84 mmol) and anhydrous formic acid (15 ml) was stirred under nitrogen at 60° C. for 2 hr. The reaction mixture was concentrated under reduced pressure and the residue was washed several times with hexane followed by a mixture of hexane-ether (1:1). The precipitated solid was filtered off and air dried to give the desired product (0.34 g, 96%). $^1$H NMR (CDCl$_3$): δ 4.65 (dd, 1H, J=2.4 and 5.0 Hz); 4.20–4.60 (m, 1H); 3.75–4.00 (m, 1H); 3.59 (dd, 1H, J=2.4 and 16 Hz); 3.38 (dd, 1H, J=5.0 and 16 Hz); 3.10–3.30 (m, 2H); 2.90–3.10 (m, 1H); 2.50–2.75 (m, 1H); 1.53 and 1.59 (2s, 3H); 1.50–2.20 (m, 13H).

EXAMPLE 15

7,7-Dihydro-2-spiro (2'-spirocyclopentyl)cyclopropyl-3-methyl-3-cephem-4-[(N-methyl-N-acetic acid)]carboxamide 1,1-dioxide Step A:

To a stirred and ice-cooled solution of 7,7-dihydro-2-spiro(2'-spirocyclopentyl)cyclopropyl-3-methyl-3-cephem-4-carboxylic acid-1,1-dioxide (Example 14, Step B, 0.51 g, 1.64 mmol) in anhydrous methylene chloride (15 ml) under nitrogen was added oxalyl chloride (0.27 g, 2.13 mmol) followed by two drops of DMF. The reaction mixture was then stirred at room temperature for 1 hr. and the volatile materials were removed under reduced pressure. The residue was redissolved in methylene chloride (15 ml) and stirred under nitrogen. A solution of tertbutylsarcosine (0.238 g, 1.64 mmol) in methylene chloride (1 ml) was added followed by triethylamine (0. 174 g, 1.72 mmol) and the reaction mixture was stirred at room temperature for 1 hr. The mixture was diluted with methylene chloride (50 ml) and washed successively with water, sodium bicarbonate solution and brine. The organic layer was dried over anhydrous sodium sulphate and evaporated in vacuo to give the crude product which was purified by silica gel column chromatography using a mixture of hexane-ethyl acetate (3:2) as eluant. The pure compound, 7,7-dihydro-2-spiro(2'-spirocyclopentyl) cyclopropyl-3-methyl-3-cephem-4-[(N-methyl-N-t-butoxycarbonylmethyl)]carboxamide-1,1-dioxide was obtained as a white foam (0.33 g, 46%). $^1$H NMR (CDCl$_3$): δ 4.89 (d, 1H, J=17.0 Hz); 4.66 (dd, 1H, J=2.5 and 5.03 Hz); 3.43 (d, 1H, J=17.0 Hz) 3.61 (dd, 1H, J=2.5 and 16.2 Hz); 3.38 (dd, 1H, J=5.0 and 16.2 Hz); 3.07 and 3.09 (2s, 3H); 1.53–2.05 (m, 9H); 1.90 (d, 1H, J=6.3 Hz); 1.74 (s, 3H); 1.47 (s, 9H).

Step B:

A mixture of 7,7-dihydro-2-spiro(2'-spirocyclopentyl)-cyclopropyl-3-methyl-3-cephem-4-[(N-methyl-N-t-butoxycarbonylmethyl) ]carboxamide-1,1-dioxide (Example 15, Step A, 0.3 g, 0.68 mmol) and anhydrous formic acid (10 ml) was stirred under nitrogen at 50° C. for 3 hr. The reaction mixture was concentrated under reduced pressure and the residue was digested several times with hexane followed by a mixture of hexane-ether (3:2). The solid was filtered off and dried to give the pure product (0.19 g, 73%). $^1$H NMR (CDCl$_3$): δ 5.20 (br, s, 1H); 4.69–4.75 (br, m, 2H); 3.35–3.91 (m, 3H); 3.13 (s, 3H); 1.68 (s, 3H); 1.57–1.90 (m, 10H).

EXAMPLE 16

7α-Methoxy-2-spiro(2'-spirocyclopentyl)cyclopropyl-3-[(2,5-dihydro-6-hydroxy-2-methyl-5-oxo-1,2,4-triazin-3-yl)thiomethyl]-3-cephem-4-[{(4-carboxy)piperidine} carboxamide]-1,1-dioxide Step A:

To a mixture of 7α-methoxy-2-spiro(2'-spirocyclopentyl)-cyclopropyl-3-methyl-3-cephem-4-[{(4-t-butoxycarbonyl)piperidine}carboxamide]-1,1-dioxide (Example 7, Step B, 5.91 g, 11.6 mmol) and N-bromosuccinimide (2.38 g, 13.4 mmol) in carbon tetrachloride (200 ml) was added AIBN (0.19 g, 1.16 mmol) and the reaction mixture was heated at 100° C. for 24 hr. The reaction mixture was cooled and filtered through Celite. The filtrate was concentrated under reduced pressure and the crude product was purified by silica gel column chromatography using a mixture of hexane-ethyl acetate (7:3) to give the pure product (2.49 g, 37%). (CDCl$_3$): δ 5.15 and 5.17 (2d, 1H, J=2.3 Hz each); 4.62 (d, 1H, J=1.7 Hz); 4.20–4.45 (m, 1H); 3.98–4.17 (m, 1H); 3.60–3.75 (m, 1H); 3.56 (s, 3H); 3.42 (d, 2H, J=11.6 Hz); 2.95–3.15 (m, 1H); 2.35–2.55 (m, 1H); 1.50–2.15 (m, 14H); 1.45 (s, 9H).

Step B:

To a solution of 7α-methoxy-2-spiro(2'-spirocyclopentyl)-cyclopropyl-3-bromomethyl-3-cephem-4-[{(4-t-butoxycarbonyl)piperidine }carboxamide]-1,1-dioxide (Example 16, Step A, 1.5 g, 2.6 mmol) in acetonitrile (30 ml) was added 2-methyl-3-mercapto- 5-oxo-6-diphenylmethoxy-1,2,4-triazine (2.08 g, 6.4 mmol) followed by triethylamine (0.797 g, 7.8 mmol). The mixture was stirred at room temperature for 72 hours. Solvent was removed under reduced pressure and the residue was purified by silica gel column chromatography using a mixture of hexane-ethyl acetate (1:1) to give the pure product (0.88 g, 41.5%). $^1$H NMR (CDCl$_3$): δ 7.24–7.45 (m, 10H); 6.75 (s, 1H); 5.14 (d, 1H, J=2.0 Hz); 4.62 (d, 1H, J=2.0 Hz); 4.20–4.40 (m, 1H); 3.50–3.90 (m, ,3H); 3.61 (s, H); 3.55 (s, 3H); 2.90–3.30 (m, 2H); 2.30–2.55 (br, m, 1H); 1.50–2.00 (m, 14H); 1.45 and 1.39 (2s, 9H).

Step C:

To a stirred and ice-cooled solution of 7α-methoxy-2-spiro(2'-spirocyclopentyl) cyclopropyl-3-[(2,5-dihydro-6-diphenylmethoxy-2-methyl-5-oxo-1,2,4-triazin-3-yl)thiomethyl]-3-cephem-4-[{(4-t-butoxycarbonyl)-piperidine}carboxamide]-1,1-dioxide (Example 16, Step B, 0.836 g, 1 mmol) in dry methylene chloride (11 ml) was added dry anisole (20 ml) followed by trifluoroacetic acid (33 ml). The mixture was stirred at 0° C. for 1 hr. and concentrated under reduced pressure. The residue was dissolved in small volume of methylene chloride and diluted with ether. The precipitated solid was filtered off and washed with hexane to give the title compound as a white powder (0.579 g, 95%). $^1$H NMR (CDCl$_3$): δ 5.16 (br, s, 1H); 4.66 (br, s, 1H); 4.30–4.45 (m, 1H); 3.75 and 3.77 (2s, 3H); 3.56 (s, 3H); 3.40–4.00 (m, 3H); 3.00–3.35 (m, 2H); 2.50–2.65 (m, 1H); 1.50–2.15 (m, 14H).

EXAMPLE 17

7α-Methoxy-2-spiro(2'-spirocyclopentyl)cyclopropyl-3-methyl-3-caphem-4-methylcarbonyl-1,1-dioxide To a stirred and ice-cooled solution of 7α-methoxy-2-spiro(2'-spirocyclopentyl)cyclopropyl-3-methyl-3-cephem-4-carboxylic acid-1,1-dioxide (Example 7, Step A, 1.0 g, 2.929 mmol) in dry methylene chloride (20 ml) was added oxalyl chloride (332 μl, 3.808 mmol) followed by two drops of DMF, the reaction mixture was stirred at ice temperature for 15 min. and then at room temperature for 3 hr. Solvent was removed under reduced pressure. The residue was dissolved in dry THF (15 ml), cooled to −78° C., cuprous iodide (587 mg, 3.076 mmol) was added in one portion followed by methyl magnesium bromide (1.27 ml, 3(M) in ether); cooling bath was removed and the mixture was stirred for 2.5 hr. Saturated NH$_4$Cl (1 ml) was added slowly to the mixture and volatile materials were removed under reduced pressure. The residue was suspended in methylene chloride and filtered through a small bed of Celite. The filtrate was washed with aq. NaHCO$_3$ solution, brine, dried over anhydrous sodium sulphate and concentrated. The crude product (800 mg) was chromatographed on a silica gel column using hexane-ethyl acetate (2:1) mixture as eluant to afford a yellow foam which on treatment with ether gave the pure compound, 7α-methoxy-2-spiro (2'-spirocyclopentyl)cyclopropyl-3-methyl-3-cephem-4-methylcarbonyl-1,1-dioxide as a white foam (418 mg, 50% yield). $^1$H NMR (CDCl$_3$): δ 5.12 (d, 1H, J=1.5 Hz); 4.62 (d, 1H, J=1.5 Hz); 3.58 (s, 3H); 2.48 (s, 3H); 1.98 (d, 1H, J=6.7 Hz); 1.72 (s, 3H); 1.61 (d, 1H, J=6.7 Hz); 1.50–1.99 (m, 8H)

EXAMPLE 18

7α-Methoxy-2-spiro(2'-spirocyclopentyl)cyclopropyl-3-methyl-3-cephem-4-[4'-(methyl)-4'-(methoxyimino)]-1,1-dioxide To a stirred suspension of 7α-methoxy-2-spiro(2'-spirocyclopentyl)cyclopropyl-3-methyl-3-cephem-4-methylcarbonyl-1,1-dioxide (Example 17, 418 mg, 1.232 retool) in a mixture of THF (8 ml) and ethanol (5 ml) was added pyridine (204 μl, 2.524 mmol) and methoxylamine hydrochloride (216 mg, 2.537 mmol). The mixture was stirred at room temperature for 4 days and then concentrated under reduced pressure. The residue was dissolved in EtOAc, then washed with water, dilute HCl, brine, dried over anhydrous Na$_2$SO$_4$, filtered and then concentrated to give a yellow foam (310 mg). The crude material was purified over a silica gel column using hexane-ethyl acetate mixture as eluant.

The fast eluting component was the minor isomer of 4-[4'-(methyl)-4'-(methoxyimino)]; 4 mg.

$^1$H NMR (CDCl$_3$): δ 4.84 (d, 1H, J=1.6 Hz); 4.53 (d, 1H, J=1.6 Hz); 3.95 (s; 3H); 3.58 (s, 3H); 2.03 (s, 3H); 1.92 (s, 3H); 1.79 (d, 1H, J=6.3 Hz); 1.50–1.90 (m, 8H); 1.43 (d, 1H, J=6.3 Hz).

The second major component was the major isomer of 4-[4'-(methyl)-4'-(methoxyimino)]; 110 mg.

$^1$H NMR (CDCl$_3$): δ 5.09 (d, 1H, J=1.9 Hz); 4.57 (d, 1H, J=1.9 Hz); 3.95 (s, 3H); 3.55 (s, 3H); 2.05 (s, 3H); 1.92 (d, 1H, J=6.5 Hz); 1.58 (s, 3H); 1.52 (d, 1H, J=6.5 Hz); 1.50–1.90 (m, 8H).

EXAMPLE 19

7α-Methoxy-2-spiro(2'-spirocyclopentyl)cyclopropyl-3-methyl-3-cephem-4-[{(4 -carboxamide)piperidine}carboxamide]-1,1-dioxide By using the same procedure as described in Example 7, Step B, but using isonipecotamide instead of 4-t-butoxycarbonyl piperidine, the title compound was prepared. $^1$H NMR (CDCl$_3$): δ 5.73 (br, 2H); 5.12 (d, 1H, J=1.6 Hz); 4.47–4.74 (m, 1H); 4.61 and 4.62 (2d, 1H, J=2.0 Hz); 3.70–4.00 (m, 1H); 3.55 and 3.54 (2s, 3H); 2.70–3.20 (m, 2H); 2.30–2.50 (m, 1H); 1.53–1.98 (m, 14H); 1.59 and 1.53 (2s, 3H).

EXAMPLE 20

7α-Methoxy-2-spiro(2'-spirocyclopentyl)cyclopropyl-3-methyl -3-cephem-4-[{(4-cyano)piperidine}carboxamide-1,1-dioxide A solution of 7α-methoxy-2-spiro(2'-spirocyclopentyl)cyclopropyl-3-methyl-3-cephem-4-[{(4-carboxamide)piperidine}carboxamide]-1,1-dioxide (Example 19, 100 mg, 0.23 mmol) in 5 ml of acetic anhydride was heated at 110°–115° C. for 18 hr. The solvent was removed under reduced pressure and the residue was dissolved in methylene chloride, washed with water aqueous NaHCO$_3$ solution, brine, dried over anhydrous Na$_2$SO$_4$, filtered and concentrated to give a light yellow foam, 75 mg (75%). $^1$H NMR (CDCl$_3$): δ 5.13 and 5.12 (2d, 1H, J=1.9 Hz); 4.61 (d, 1H, J=1.9 Hz); 4.00–4.20 (m, 1H); 3.20–3.70 (m, 3H); 3.54 and 3.56 (2s, 3H); 2.90–3.00 (m, 1H); 1.60–2.10 (m, 14H); 1.53 and 1.56 (2s, 3H).

EXAMPLE 21

7α-Methoxy-2-spiro(2'-spirocyclopentyl)cyclopropyl-3-methyl-3-cephem-4-[{(4-hydroxy)piperidine}carboxamide]-1,1-dioxide By using the same procedure as described in Example 7, Step B, but using 4-hydroxy piperidine instead of 4-t-butoxycarbonyl piperidine, the title compound was prepared. $^1$H NMR (CDCl$_3$): δ 5.12 and 5.13 (2d, 1H, J=1.7 Hz); 4.61 (d, 1H, J=1. 7 Hz); 3.90–4.30. (m, 2H); 3.60–3.85 (m, 1H); 3.53 and 3.55 (2s, 3H); 3.15–3.40 (m, 2H); 1.48–2.00 (m, 14H); 1.54 and 1.57 (2s, 3H).

EXAMPLE 22

7α-Methoxy-2-spiro(2'-spirocyclopentyl)cyclopropyl-3-methyl-3-cephem-4-[{(4-hydroxyethyl)piperidine}carboxamide]-1,1-dioxide By using the same procedure as described in Example 7, Step B, but using 4-hydroxyethyl piperidine instead of 4-t-butoxycarbonyl piperidine, the title compound was prepared. $^1$H NMR (CDCl$_3$): δ 5.12 (2d, 1H, J=1.5 Hz); 4.55–4.70 (m, 1H); 4.62 and 4.64 (2d, 1H, J=1.9 Hz); 3.75–3.98 (m, 1H); 3.71 (t, 2H, J=6.4 Hz); 3.53 and 3.54 (2s, 3H); 2.64–3.15 (m, 2H); 1.50–2.18 (m, H); 1.52 and 1.60 (2s, 3H).

EXAMPLE 23

7α-Methoxy,2-spiro(2'-spirocyclopentyl)cyclopropyl-3-methyl-3-cephem-4-[{(4-bromoethyl)piperidine}carboxamide]-1,1-dioxide Bromine (23 μl, 0.45 mmol) was added to a vigorously stirred solution of triphenylphosphine (123 mg, 0.468 mmol) in 3 ml of dry CH$_3$CN. A solution of 7α-methoxy-2-spiro(2'-spirocyclopentyl) cyclopropyl-3-methyl-3-cephem-4- [{(4-hydroxyethyl) piperidine}carboxamide]-1,1-dioxide (Example 22, 200 mg, 0.442 mmol) in 2 ml of CH$_3$CN was added to the mixture and the mixture was stirred at room temperature overnight. Solvent was removed under reduced pressure and the residue was purified over a silica gel column using hexane-ethyl acetate mixture as eluant. The title compound was obtained as a light yellow foam, 220 mg (97%). $^1$H NMR (CDCl$_3$): δ 5.12 (d, 1H, J=1.9 Hz); 4.55-4.73 (m, 1H); 4.59 and 4.61 (2d, 1H, J=2.0 Hz); 3.70–3.90 (m, 1H); 3.54 (2s, 3H); 3.38–3.48 (m, 2H); 2.60–3.20 (m, 2H); 1.42–1.98 (m, 17H); 1.51 and 1.59 (2s, 3H).

EXAMPLE 24

7α-Methoxy-2-spiro(2'-spirocyclopentyl)cyclopropyl-3-methyl-3-cephem-4-[{(4-diethoxyphosphinylethyl)-piperidine}carboxamide]-1,1-dioxide A solution of 7α(-methoxy-2-spiro(2'-spirocyclopentyl)cyclopropyl-3-methyl-3-cephem-4-[{(4-bromoethyl)piperidine}carboxamide]-1,1-dioxide (Example 23, 660 mg, 1.28 mmol) in 4.7 ml of triethyl phosphite was heated at 110° C. for 18 hr. Excess triethyl phosphite was removed under reduced pressure and the residue was purified over a silica gel column using ethyl acetate-methanol mixture as eluant to afford the product as a white foam; 300 mg (41%). $^1$H NMR (CDCl$_3$): δ 5.12 and 5.13 (2d, 1H, J=1.7 Hz); 4.56–4.70 (m, 1H); 4.60 and 4.61 (2d, 1H, J=1.9 Hz); 4.02–4.17 (m, 4H); 3.70–3.95 (m, 1H); 3.54 and 3.55 (2s, H); 2.58–3.15 (m, 2H); 1.50–2.00 (m, 19H); 1.51 and 1.59 (2s, H); 1.32 (t, 6H, J=7.0 Hz).

What is claimed is:

1. A 7α-subsituted 2-spiro(2'-spirocycloalkyl)cyclopropyl cephalosporin sulfone of the structural formula (I)

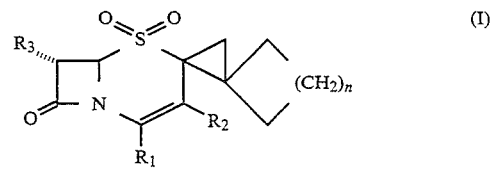

wherein R$_1$ is COOR$_4$, COR$_5$, C(R$_5$)=N-OR$_6$ in which OR$_6$ is in the "syn" configuration or the "anti" configuration, CONR-R$_8$;

R$_4$ is hydrogen; C$_{1-6}$ branched or stratight chain alkyl; C$_{2-6}$ alkenyl; C$_{1-6}$ alkanoyl C$_{1-6}$ alkyl; C$_{1-6}$ alkanoyloxy C$_{1-6}$ alkyl; C$_{1-6}$ alkoxy C$_{1-6}$ alkyl; halogenated C$_{1-6}$ alkyl; -CH$_2$-phenyl; -CH(phenyl)$_2$; the phenyl groups being unsubstituted or substituted with at least one of C$_{1-6}$ alkyl, C$_{1-6}$ alkoxy, and nitro;

R$_5$ is hydrogen; C$_{1-6}$ straight or branched chain alkyl; C$_{2-6}$ alkenyl; C$_{2-6}$ alkynyl; C$_{3-6}$ cycloalkyl; C$_{6-10}$ aryl; aralkyl; thienyl; furyl; pyridyl; pyrimidinyl; imidazolyl; triazinyl; triazolyl; thiazolyl; thiadiazolyl; thienylmethyl; furylmethyl; pyridylmethyl triazolylmethyl; thiazolylmethyl; thiadiazolylmethyl;

R$_6$ is hydrogen or a C$_{1-6}$ straight or branched alkyl, which can be unsubstituted or substituted with -COOH, -COOC$_{1-6}$alkyl, R$_7$ and R$_8$ are the same or different, and are selected from hydrogen; C$_{1-6}$ alkyl; C$_{3-6}$ cycloalkyl; C$_{6-10}$ aryl; C$_{7-12}$ aralkyl; C$_{1-6}$ alkoxycarbonyl C$_{1-6}$ akyl; carboxyl C$_{1-6}$ alkyl;

or R$_7$ and R$_8$ in the formula CONR$_7$R$_8$ may combine to form part of a heterocyclic ring containing 3–7 carbon atoms with the nitrogen atom to which they are bound, wherein the heterocylic ring may contain one or more additional heteroatom selected from the group consisting of N, S and O, and wherein the ring is unsubstituted or substituted at a carbon atom or at a nitrogen atom with C$_{1-6}$alkyl, -COOC$_{1-6}$alkyl, -COOH, -CH$_2$COOC$_{1-6}$alkyl, -CH$_2$COOH, hydroxy, cyano, carboxamide, hydroxyethyl, haloethyl, or diethoxyphosphinylethyl;

R$_2$ is hydrogen, chloro, bromo, fluoro, hydroxy, C$_{1-6}$ alkoxy, trifluoromethyl, C$_{1-6}$ alkyl, C$_{2-6}$ alkenyl, C$_{2-6}$ alkynyl, C$_{3-6}$ cycloalkyl, or -CH$_2$X wherein X is hydroxy, chloro, bromo, C$_{1-6}$ alkoxy, C$_{1-6}$ alkanoyloxy, -OCONH$_2$, -OCONHC$_{1-6}$ alkyl, amino, -NHC$_{1-6}$ alkyl, -N(C$_{1-6}$ alkyl)$_2$; or R$_2$ is -CH$_2$YR$_9$, wherein Y is S or N, wherein when Y is sulfur, R$_9$ is hydrogen, a phenyl group or a 5 to 6 membered heterocyclic group containing 1 to 4 nitrogen atoms, with or without sulfur or oxygen and when Y is nitrogen, R$_9$ together with Y forms a nitrogen containing heterocylcic ring selected from triazolyl group, pyridinium group, N-methyl pyrrolidinium group, or N-methyl piperidinium group;

n is 0, 1, 2, 3 or 4;
R$_3$ is hydrogen or C$_{1-6}$ alkoxy;
or a pharmaceutically acceptable salt or ester thereof.

2. A 7 α-substituted 2'-spirocycloalkyl-2-spirocyclopropyl cephalosporin sulfone of formula (I)

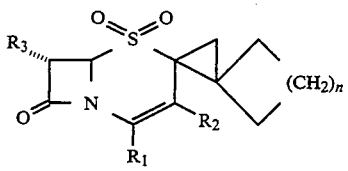

wherein R$_1$ is COOR$_4$, COR$_5$, C(R$_5$)=N-OR$_6$, CONR$_7$R$_8$;
R$_4$ is hydrogen, C$_{1-6}$ alkyl or -CH(phenyl)$_2$
R$_5$ is hydrogen, C$_{1-6}$ alkyl or C$_{6-10}$aryl
R$_6$ is hydrogen or C$_{1-6}$ alkyl
R$_7$ and R$_8$ are the same or different and are hydrogen, C$_{1-6}$ alkyl or carboxyl C$_{1-6}$ alkyl
or NR$_7$R$_8$ in the formula CONR$_7$R$_8$ form part of a heterocyclic ring containing 3-7 carbon atoms with the N to which they are bound, wherein the heterocyclic ring may contain one or more additional heteroatoms selected from the group consisting of N, S or O and wherein the ring is unsubstituted or substituted at a carbon atom or a nitrogen atom with one of the groups consisting of C$_{1-6}$alkyl; -COOC$_{1-6}$alkyl; -COOH: -CH$_2$COOC$_{1-6}$alkyl, -CH$_2$COOH, hydroxy, hydroxyethyl, cyano, carboxamide, haloethyl and diethoxyphosphinylethyl
R$_2$ is C$_{1-6}$alkyl which is unsubstituted or substituted by halogen or C$_{2-6}$alkanoyloxy or R$_2$ is -CH$_2$SR$_9$;
R$_9$ is a 5 or 6 membered heterocyclic ring group containing 1 to 4 nitrogen atoms, with or without sulfur or oxygen and the ring is unsubstituted or substituted with one or more radicals selected from C$_{1-6}$alkyl, -COOH, -COOC$_{1-6}$alkyl, -OH, -CH$_2$COOH, -CH$_2$COOC$_{1-6}$ alkyl or halogen;
R$_3$ is hydrogen or C$_{1-6}$alkoxy
n is 0, 1, 2, 3, or 4,
or a pharmaceutically acceptable salt thereof.

3. A compound according to claim 1 which is selected from the group consisting of:

t-butyl-7 α-methoxy-2-spiro(2'-spirocyclopentyl)cyclopropyl-3-methyl-3-cephem-4-carboxylate-1,1-dioxide;

t-butyl-7 α-methoxy-2-spiro(2'-spirocyclohexyl)cyclopropyl-3-methyl-3-cephem-4-carboxylate-1,1-dioxide;

7 α-Methoxy-2-spiro(2'-spirocyclopentyl)cyclopropyl-3-methyl-3-cephem-4-carboxylic acid-1,1-dioxide and its sodium salt;

7 α-Methoxy-2-spiro(2'-spirocyclohexyl)cyclopropyl-3-methyl-3-cephem-4-carboxylic acid-1,1-dioxide and its sodium salt;

t-butyl -7α-(methoxy-2-spiro(2'-spirocyclopentyl)cyclopropyl-3-acetoxymethyl-3-cephem-4-carboxylate-1,1-dioxide;

7 α-methoxy-2 -spiro(2'-spirocyclopentyl)cyclopropyl-3-methyl-3 -cephem-4- [ {(4 -N-methyl)-piperazine}carboxamide]-1,1-dioxide and its hydrochloride salt;

7 α-methoxy-2-spiro(2'-spirocyclopentyl)cyclopropyl-3-methyl-3-cephem-4-[{(4-t-butoxycarbonyl)-piperidine}carboxamide]-1,1-dioxide;

7 α-methoxy-2-spiro(2'-spirocyclopentyl)cyclopropyl-3-methyl-3-cephem-4-[{(4-carboxy)-piperidine)carboxamide]-1,1-dioxide and its sodium salt;

7 α-methoxy-2-spiro(2'-spirocyclopentyl)cyclopropyl-3-methyl-3-cephem-4-[{(4-N-t-butoxycarbonylmethyl)piperazine}carboxamide]-1,1-dioxide;

7 α-methoxy-2-spiro(2 '-spirocyclopentyl)cyclopropyl-3-methyl-3 -cephem-4-[{(4-N-acetic acid)-piperazine}carboxamide]-1,1-dioxide and its sodium salt;

7 α-methoxy-2-spiro(2'-spirocyclohexyl)cyclopropyl-3-methyl-3-cephem-4-[{(4-N-methyl)-piperazine)carboxamide]-1,1-dioxide and its hydrochloride salt;

7 α-methoxy-2-spiro(2'-spirocyclohexyl)cyclopropyl-3-methyl-3-cephem-4-[{(4-N-t-butoxycarbonylmethyl)piperazine)}carboxamide]-1,1-dioxide;

7 α-methoxy-2-spiro(2'-spirocyclohexyl)cyclopropyl-3-methyl-3-cephem-4-[{(4-N-acetic acid)-piperazine}carboxamide]-1,1-dioxide and its sodium salt;

t-butyl-7 α-methoxy-2-spiro(2'-spirocyclopentyl)cyclopropylbromomethyl-3-cephem-4-carboxylate-1,1-dioxide;

t-butyl-7 α-methoxy-2 -spiro(2'-spirocyclopentyl)cyclopropyl-3-[(2,5-dihydro-6-hydroxy-2-methyl-5-oxo-1,2,4-triazin-3-yl)thiomethyl]-3-cephem-4-carboxylate-1,1-dioxide and its sodium salt;

t-butyl-7 α-methoxy-2-spiro(2'-spirocyclopentyl)cyclopropyl-3-[(1-methyl-1,2,3,4-tetrazole-5-yl)thiomethyl]-3-cephem-4-carboxylate-1,1-dioxide;

t-butyl-7 α-methoxy-2-spiro(2'-spirocyclopentyl)cyclopropyl-3-[(2-methyl-1,3,4-thiadiazole-5-yl)thiomethyl]-3-cephem-4-carboxylate-1,1-dioxide;

t-butyl-7 α-methoxy-2-spiro(2'-spirocyclopentyl)cyclopropyl-3-[(pyridyl-2-yl)thiomethyl]-3-cephem-4-carboxylate-1,1-dioxide;

t-butyl-7 α-methoxy-2-spiro(2'-spirocyclopentyl)cyclopropyl-3-[(pyridyl-4-yl)thiomethyl]-3-cephem-4-carboxylate-1,1-dioxide;

7 α-methoxy-2-spiro(2'-spirocyclopentyl)cyclopropyl-3-[(2,5-dihydro-6-hydroxy-2-methyl-5-oxo-1,2,4-triazin-3yl)thiomethyl]-3-cephem-4-piperidine carboxamide-1,1-dioxide, and its sodium salt;

7,7 -dihydro-2-spiro(2'-spirocyclopentyl)cyclopropyl-3-methyl-3-cephem-4-[{(4-carboxy)piperidine}carboxamide]-1,1-dioxide, and its sodium salt;

7,7-dihydro-2-spiro(2'-spirocyclopentyl)cyclopropyl-3-methyl-3-cephem-4-[(N-methyl-N-acetic acid)-]carboxamide-1,1-dioxide, and its sodium salt;

7 α-methoxy-2-spiro(2'-spirocyclopentyl)cyclopropyl-3-[(2,5-dihydro-6-hydroxy-2-methyl-5-oxo-1,2,4-triazin-3-yl)thiomethyl]-3-cephem-4-[{(4-carboxy) piperidine)-carboxamide]-1,1-dioxide, and its sodium salt;

7 α-methoxy-2-spiro(2'-spirocyclopentyl)cyclopropyl-3-methyl-3-cephem-4-methylcarbonyl-1,1-dioxide;

7 α-methoxy-2-spiro(2'-spirocyclopentyl)cyclopropyl-3-methyl-3-cephem-4-[4 '-(methyl)-4'-(methoxyimino)]-1,1-dioxide;

7 α-methoxy-2 -spiro(2'-spirocyclopentyl)cyclopropyl-3-methyl-3-cephem-4-[{(4-carboxamide)-piperidine)carboxamide]-1,1- dioxide;

7 α-methoxy-2 -spiro(2'-spirocyclopentyl)cyclopropyl-3-methyl-3-cephem-4-[{(4-cyano)piperidine)-carboxamide]-1,1-dioxide;

7 α-methoxy-2-spiro(2'-spirocyclopentyl)cyclopropyl-3-methyl-3-cephem-4-[{(4-hydroxy)-piperidine}carboxamide]-1,1-dioxide;

7 α-methoxy-2-spiro(2'-spirocyclopentyl)cyclopropyl-3-methyl-3-cephem-4-[{(4-hydroxyethyl)-piperidine}carboxamide]-1,1-dioxide;

7 α-methoxy-2-spiro(2'-spirocyclopentyl)cyclopropyl-3-methyl-3-cephem-4-[{(4-bromoethyl)-piperidine}carboxamide]-1,1-dioxide; and 7 α-methoxy-2-spiro(2'-spirocyclopentyl)cyclopropyl-3-methyl-3-cephem-4- [{(4-diethoxyphosphinylethyl) piperidine}carboxamide]-1,1-dioxide.

4. A compound as recited in claim 1, wherein said hydrocarbon residue substituent is selected from the group consisting of $C_{3-6}$ cycloalkyl, carboxyl, $C_{1-8}$ alkoxycarbonyl, $C_{6-10}$ aryl, thienyl; furyl; pyridyl; triazolyl; thiazolyl; and thiadiazolyl.

5. A compound as recited in claim 1, wherein $R_7$ and $R_8$ in the formula $CONR_7R_8$ combine to form a heterocyclic ring containing 3-7 carbon atoms with the N to which they are bound, wherein the heterocyclic ring may contain at least one other heteroatom selected from N, S and O, said heterocyclic ring component being substituted with one or more substituents selected from the group consisting of hydroxy, carboxy, tert-butoxycarbonyl, azido, amino, hydroxymethyl, hydroxyethyl, bromoethyl, bromomethyl, cyano, carboxamide, guanidino, diethylphosphinylmethyl, diethylphosphinylethyl, dihydroxyphosphinylmethyl, dihydroxyphosphinylethyl, 1,2,3-triazole, tetrazole.

6. A compound as recited in claim 1, wherein said quaternary ammonium group is selected from the group consisting of $N^{\oplus}H_3$, $N^{\oplus}HZ_2$, $N^{\oplus}Z_3$, where Z is lower alkyl, aryl or aralkyl, or a pyridinium group: N-methyl pyrrolidinium group, or N-methyl piperidinium group.

7. A compound as recited in claim 1, wherein n is 1, 2 or 3.

8. A compound as recited in claim 1, wherein $R_3$ is methoxy or ethoxy.

9. A compound as recited in claim 1, wherein said hydrocarbon residue is $C_{1-6}$ straight or branched chain alkyl, $C_{2-6}$ alkenyl or $C_{3-6}$ cycloalkyl.

10. A pharmaceutical composition for controlling inflammatory or degenerative conditions in a mammal comprising an effective amount of at least one 2-spiro(2'-spirocycloalkyl)cyclopropyl cephalosporin sulfone of the structural formula (I) as defined in claim 1 or a pharmaceutically acceptable salt or ester thereof, in admixture with a pharmaceutically acceptable carrier.

11. A method of treating inflammatory or degenerative conditions which comprises administering to a patient in need of such treatment an effective amount of a cephalosporin sulfone of the formula (I) as defined in claim 1.

12. A method as recited in claim 11, wherein said patient is an animal or a human being.

* * * * *